(12) United States Patent
Murray et al.

(10) Patent No.: US 8,962,569 B2
(45) Date of Patent: Feb. 24, 2015

(54) COMPOSITIONS COMPRISING SPP24 PEPTIDE FRAGMENTS

(75) Inventors: Samuel S. Murray, Saugus, CA (US); Elsa J. Murray, Saugus, CA (US); Jeffrey C. Wang, Sherman Oaks, CA (US)

(73) Assignees: The Regeants of the University of California, Oakland, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/699,288

(22) PCT Filed: May 25, 2011

(86) PCT No.: PCT/US2011/037952
§ 371 (c)(1), (2), (4) Date: Feb. 5, 2013

(87) PCT Pub. No.: WO2011/150094
PCT Pub. Date: Dec. 1, 2011

(65) Prior Publication Data
US 2013/0143811 A1 Jun. 6, 2013

Related U.S. Application Data

(60) Provisional application No. 61/348,205, filed on May 25, 2010.

(51) Int. Cl.
C07K 14/00 (2006.01)
C07K 9/00 (2006.01)
A61K 38/04 (2006.01)
A61K 38/16 (2006.01)
A61K 38/17 (2006.01)

(52) U.S. Cl.
CPC .................. *A61K 38/1709* (2013.01)
USPC ........ 514/21.3; 514/21.4; 514/19.2; 530/300; 530/324; 530/326; 424/468

(58) Field of Classification Search
None
See application file for complete search history.

(56) References Cited

FOREIGN PATENT DOCUMENTS

WO    WO 96-21006    7/1996

OTHER PUBLICATIONS

Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Lawrence et al. (1999, Anti-Cancer Drugs 10:655-661).*
Hanauske et al. (1995, Investigational New Drugs 13: 43-49).*
Kornblith et al. (2003, Anticancer Research 23:543-548).*
Depenbrock et al. (1997, European Journal of Cancer 33:2404-2410).*
Gabrielson et al. (1999, Clinical Cancer Research 5:1638-1641).*
Georgoulias (2002, Current Medicinal Chemistry 9:869-877).*
Burris III et al. (1992, Journal of the National Cancer Institute 84:1816-1820).*
Martin et al. (1994, Journal of the National Cancer Institute 86:608-613).*
Izbicka et al. (1999, investigational New Drugs 16:221-225).*
International Search Report for appl. PCT/US2011/037952, mailed Mar. 2, 2012, 4 pgs.
Brochmann et al., "Carboxy terminus of secreted phosphoprotein-24 kDa (spp24) is essential for full inhibition of BMP-2 activity", J. of Orthopedic Res. Epub. vol. 28, No. 9, pp. 1200-1207 (2010).
Freeley et al., "Mixed Metastatic Lung Cancer Lesions in Bone are Inhibited by Noggin Overexpression and Rank: Fc Administration", J. of Bone and Mineral Res. vol. 21, issue 10, pp. 1571-1580 (2006).
Lee et al., "Effects of the bone morphogenetic protein binding protein spp24 (secreted phosphoprotein 24KD) on the growth of human lung cancer cells", J. of Orthopedic Res. Epub, vol. 29, No. 11 pp. 1712-1718 (2011).

* cited by examiner

*Primary Examiner* — Elizabeth C Kemmerer
(74) *Attorney, Agent, or Firm* — Bret E. Field; Bozicevic, Field & Francis LLP

(57) ABSTRACT

Provided herein is tumor suppression composition and methods of making and using the same.

8 Claims, 10 Drawing Sheets

```
         +2                         SEQ ID NO.:1    M   H   H   H   H   H   H   F
       3401                                       NdeI
                                                  ~~~~~~
SEQ ID NO.:2  GTTTAACTTT AAGAAGGAGA TATACATATG CACCACCACC ACCACCACTT
SEQ ID NO.:33 CAAATTGAAA TTCTTCCTCT ATATGTATAC GTGGTGGTGG TGGTGGTGAA

+2   P V Y      D Y D P    A S L       K E A     L S A
       3451  CCCGGTGTAT GACTATGACC CGGCTTCCCT GAAGGAGGCT CTCAGCGCCT
             GGGCCACATA CTGATACTGG GCCGAAGGGA CTTCCTCCGA GAGTCGCGGA

+2 S V A K      V N S      Q S L S     P Y L     F R A
       3501  CTGTGGCAAA AGTGAATTCC CAGTCACTGA GCCCCTATCT GTTTCGGGCG
             GACACCGTTT TCACTTAAGG GTCAGTGACT CGGGGATAGA CAAAGCCCGC

+2   F R S S    V K R      V N A       L D E D    S L T
       3551  TTTAGAAGCT CAGTTAARAG AGTCAACGCC CTGGACGAGG ACAGCTTGAC
             AAATCTTCGA GTCAATTTTC TCAGTTGCGG GACCTGCTCC TGTCGAACTG

+2   M D L      E F R I    Q E T       T C R     R E S
       3601  CATGGACTTA GAGTTCAGGA TTCAAGAGAC GACGTGCAGG AGGGAATCTG
             GTACCTGAAT CTCAAGTCCT AAGTTCTCTG CTGCACGTCC TCCCTTAGAC

+2   E A D P    A T C      D F Q R     G Y H     V P V
       3651  AGGCAGACCC CGCCACCTGT GACTTCCAGA GGGGCTACCA CGTGCCCGTG
             TCCGTCTGGG GCGGTGGACA CTGAAGGTCT CCCCGATGGT GCACGGGCAC

+2   A V C R    S T V      R M S       A E Q V    Q N V
       3701  GCCGTTTGCA GAAGCACCGT GCGGATGTCT GCTGAACAGG TGCAGAACGT
             CGGCAAACGT CTTCGTGGCA CGCCTACAGA CGACTTGTCC ACGTCTTGCA

+2   W V R      C H W S    S S S       G S S     S S E
       3751  GTGGGTTCGC TGCCACTGGT CCTCCAGCTC TGGGTCCAGC AGCAGTGAAG
             CACCCAAGCG ACGGTGACCA GGAGGTCGAG ACCCAGGTCG TCGTCACTTC

+2 E M F F      G D I      L G S S     T S R     N S Y
       3801  AGATGTTTTT TGGGGATATC TTGGGATCCT CTACATCAAG AAACAGTTAC
             TCTACAAAAA ACCCCTATAG AACCCTAGGA GATGTAGTTC TTTGTCAATG

+2   L L G L    T P D      R S R       G E P L    Y E P
       3851  CTGCTTGGCC TCACTCCTGA CAGATCCAGA GGTGAACCAC TTTATGAACC
             GACGAACCGG AGTGAGGACT GTCTAGGTCT CCACTTGGTG AAATACTTGG

+2   S R E      M R R N    F P L       G N R     R Y S
       3901  ATCACGTGAG ATGAGAAGAA ACTTTCCTCT TGGAAATAGA AGGTACTCGA
             TAGTGCACTC TACTCTTCTT TGAAAGGAGA ACCTTTATCT TCCATGAGCT

+2 N P W P      R A R      V N P G     F E  *    *
                                                       HindIII
                                                       ~~~~~~
       3951  ACCCGTGGCC CAGAGCAAGA GTAAACCCTG GCTTTGAGTG ATAAGCTTGC
             TGGGCACCGG GTCTCGTTCT CATTTGGGAC CGAAACTCAC TATTCGAACG
```

FIG. 2

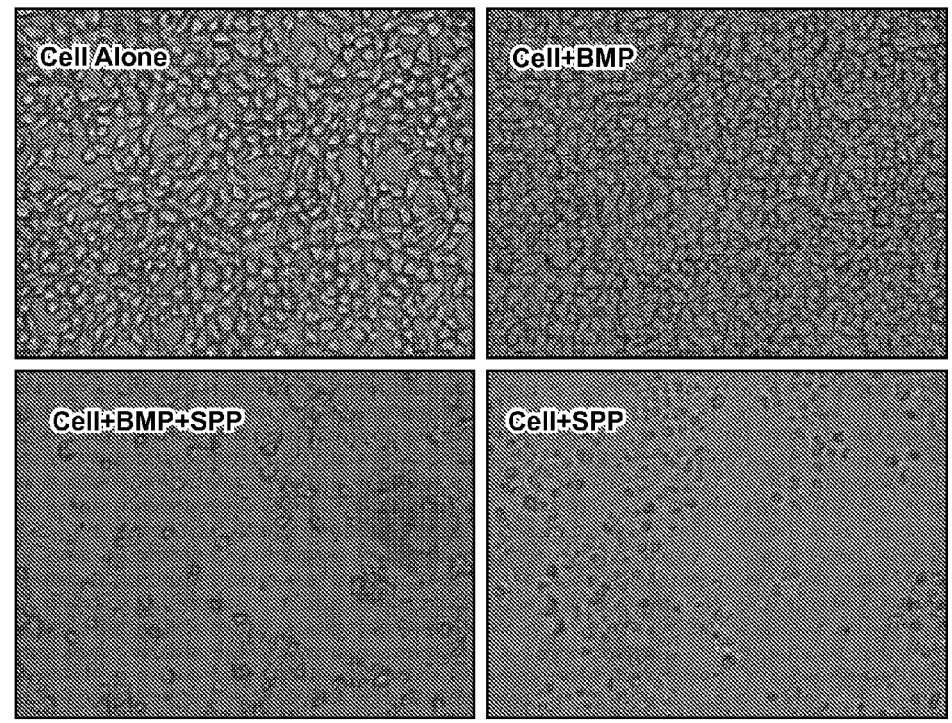
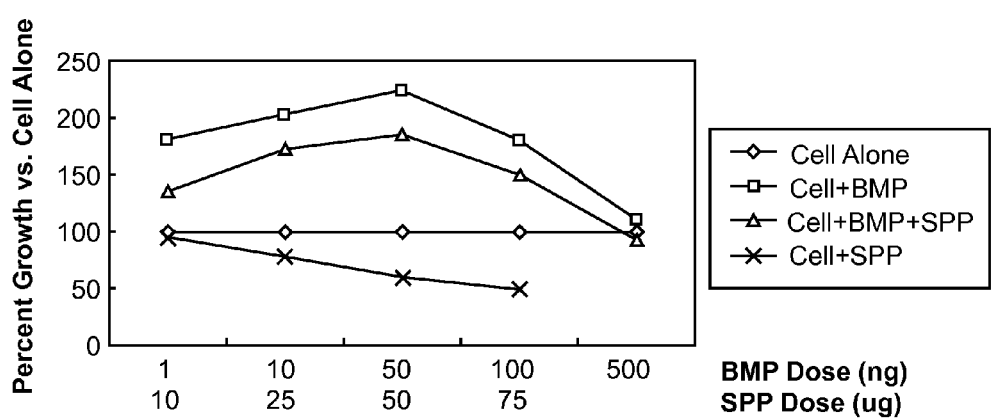
FIG. 7

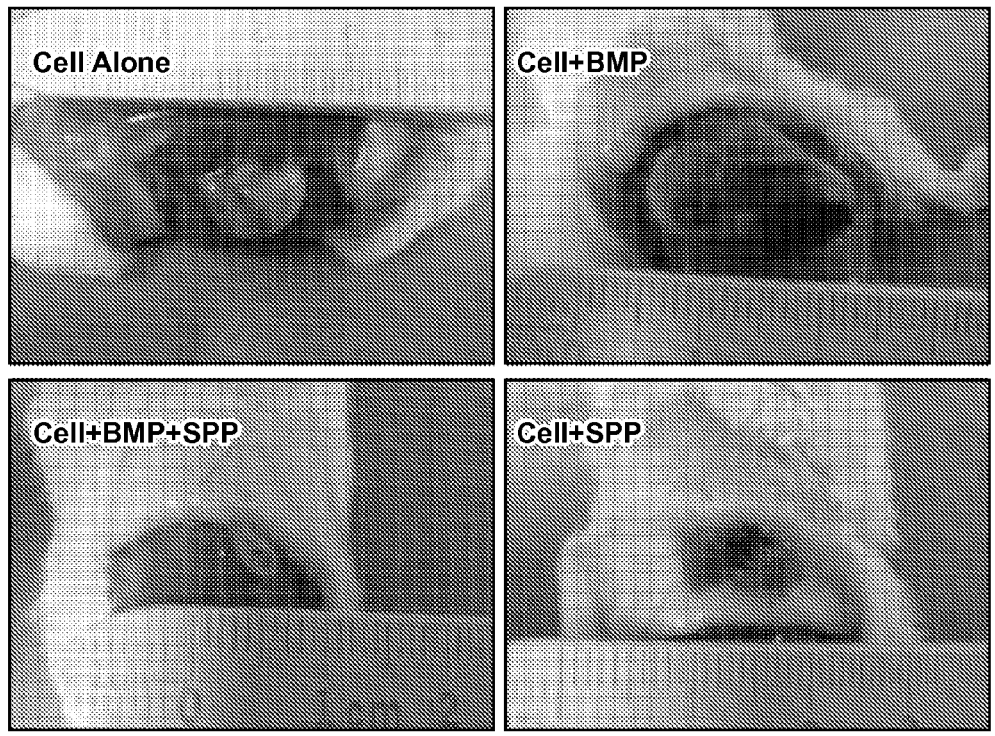
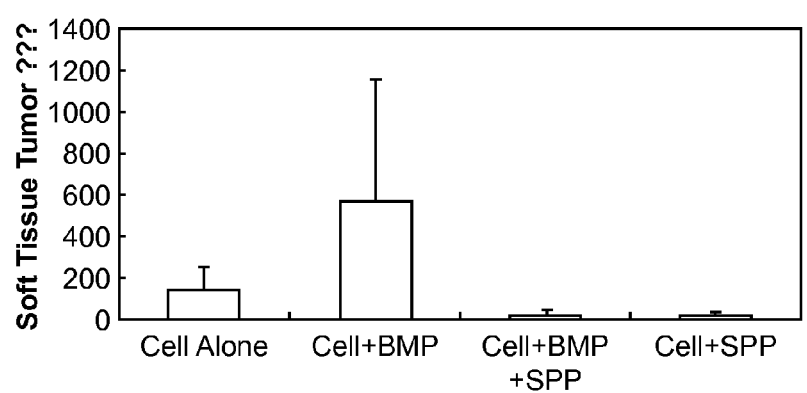
FIG. 8

SEQUENCE LISTING

<160> NUMBER OF SEQ ID NOS: 35

<210> SEQ ID NO 1
<211> LENGTH: 187
<212> TYPE: PRT
<213> ORGANISM: Artificial Sequence
<220> FEATURE:
<223> OTHER INFORMATION: Synthetic spp24

<400> SEQUENCE: 1

Met His His His His His Phe Pro Val Tyr Asp Tyr Asp Pro Ala
1               5                   10                  15

Ser Leu Lys Glu Ala Leu Ser Ala Ser Val Ala Lys Val Asn Ser Gln
            20                  25                  30

Ser Leu Ser Pro Tyr Leu Phe Arg Ala Phe Arg Ser Ser Val Lys Arg
        35                  40                  45

Val Asn Ala Leu Asp Glu Asp Ser Leu Thr Met Asp Leu Glu Phe Arg
    50                  55                  60

Ile Gln Glu Thr Thr Cys Arg Arg Glu Ser Glu Ala Asp Pro Ala Thr
65                  70                  75                  80

Cys Asp Phe Gln Arg Gly Tyr His Val Pro Val Ala Val Cys Arg Ser
                85                  90                  95

Thr Val Arg Met Ser Ala Glu Gln Val Gln Asn Val Trp Val Arg Cys
            100                 105                 110

His Trp Ser Ser Ser Ser Gly Ser Ser Ser Glu Glu Met Phe Phe
        115                 120                 125

Gly Asp Ile Leu Gly Ser Ser Thr Ser Arg Asn Ser Tyr Leu Leu Gly
    130                 135                 140

Leu Thr Pro Asp Arg Ser Arg Gly Glu Pro Leu Tyr Gly Pro Ser Arg
145                 150                 155                 160

Glu Met Arg Arg Asn Phe Pro Leu Gly Asn Arg Arg Tyr Ser Asn Pro
                165                 170                 175

Trp Pro Arg Ala Arg Val Asn Pro Gly Phe Glu
            180                 185

<210> SEQ ID NO 2
<211> LENGTH: 600
<212> TYPE: DNA
<213> ORGANISM: Artificial Sequence
<220> FEATURE:
<223> OTHER INFORMATION: Synthetic SPP24

<400> SEQUENCE: 2
gtttaacttt aagaaggaga tatacatatg caccaccacc accaccactt cccggtgtat      60
gactatgacc cggcttccct gaaggaggct ctcagcgcct ctgtggcaaa agtgaattcc     120
cagtcactga gccctatct gtttcgggcg tttagaagct cagttaaag agtcaacgcc     180 ctggacgagg acagcttgac catggactta gagttcagga ttcaagagac gacgtgcagg     240
agggaatctg aggcagaccc cgccacctgt gacttccaga ggggctacca cgtgcccgtg     300
gccgtttgca aagcaccgt gcggatgtct gctgaacagg tgcagaacgt gtgggttcgc     360
tgccactggt cctccagctc tgggtccagc agcagtgaag atgtttttt tggggatatc     420 ttgggatcct ctacatcaag aaacagttac ctgcttggcc tcactcctga cagatccaga     480
ggtgaaccac tttatgaacc atcacgtgag atgagaagaa actttcctct tggaaataga     540
aggtactcga acccgtggcc cagagcaaga gtaaaccctg gctttgagtg ataagcttgc     600

```
<210> SEQ ID NO 3
<211> LENGTH: 40
<212> TYPE: PRT
<213> ORGANISM: Artificial Sequence
<220> FEATURE:
<223> OTHER INFORMATION: Synthetic peptide

<400> SEQUENCE: 3

Met Glu Lys Met Ala Met Lys Met Leu Val Ile Phe Val Leu Gly Met
1               5                   10                  15

Asn His Trp Thr Cys Thr Gly Phe Pro Val Tyr Asp Tyr Asp Pro Ala
            20                  25                  30

Ser Leu Lys Glu Ala Leu Ser Ala
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic peptide

<400> SEQUENCE: 4

Ser Val Ala Lys Val Asn Ser Gln Ser Leu Ser Pro Tyr Leu Phe Arg
1               5                   10                  15

Ala Phe Arg Ser Ser Val Lys Arg Val Asn Ala Leu Asp Glu Asp Ser
            20                  25                  30

Leu Thr Met Asp Leu Glu Phe Arg
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic peptide

<400> SEQUENCE: 5

Ile Gln Glu Thr Thr Cys Arg Arg Glu Ser Glu Ala Asp Pro Ala Thr
1               5                   10                  15

Cys Asp Phe Gln Arg Gly Tyr His Val Pro Val Ala Val Cys Arg Ser
            20                  25                  30

Thr Val Arg Met Ser Ala Glu Gln
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic peptide

<400> SEQUENCE: 6

Val Gln Asn Val Trp Val Arg Cys His Trp Ser Ser Ser Ser Gly Ser
1               5                   10                  15

Ser Ser Ser Glu Glu Met Phe Phe Gly Asp Ile Leu Gly Ser Ser Thr
            20                  25                  30

Ser Arg Asn Ser Tyr Leu Leu Gly
        35                  40

<210> SEQ ID NO 7
<211> LENGTH: 43
<212> TYPE: PRT
```

<213> ORGANISM: Artificial Sequence
<220> FEATURE:
<223> OTHER INFORMATION: Synthetic peptide

<400> SEQUENCE: 7

Leu Thr Pro Asp Arg Ser Arg Gly Glu Pro Leu Tyr Glu Pro Ser Arg
1               5                   10                  15

Glu Met Arg Arg Asn Phe Pro Leu Gly Asn Arg Arg Tyr Ser Asn Pro
            20                  25                  30

Trp Pro Arg Ala Arg Val Asn Pro Gly Phe Glu
        35                  40

<210> SEQ ID NO 8
<211> LENGTH: 19
<212> TYPE: PRT
<213> ORGANISM: Artificial Sequence
<220> FEATURE:
<223> OTHER INFORMATION: Synthetic peptide

<400> SEQUENCE: 8

Cys Arg Ser Thr Val Arg Met Ser Ala Glu Gln Val Gln Asn Val Trp
1               5                   10                  15

Val Arg Cys

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Cys Cys Cys Glu Glu Glu Glu Cys His His His His Glu Glu Glu Glu
1               5                   10                  15

Glu Glu Cys

<210> SEQ ID NO 10
<211> LENGTH: 19
<212> TYPE: PRT
<213> ORGANISM: Artificial Sequence
<220> FEATURE:
<223> OTHER INFORMATION: Synthetic peptide

<400> SEQUENCE: 10

Cys Cys Glu Glu Glu Glu Glu Cys Cys Cys Glu Glu Glu Glu Glu Glu
1               5                   10                  15

Glu Cys Cys

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide

<400> SEQUENCE: 11

Cys Val Ala Val Trp Arg Lys Asn Asp Glu Asn Ile Thr Leu Glu Tyr
1               5                   10                  15

Val Cys

<210> SEQ ID NO 12
<211> LENGTH: 18
<212> TYPE: PRT

```
<213> ORGANISM: Artificial Sequence
<220> FEATURE:
<223> OTHER INFORMATION: Synthetic peptide

<400> SEQUENCE: 12

Cys Glu Glu Glu Glu Glu Cys Cys Cys Cys Glu Glu Glu Glu Glu
1               5                   10                  15

Glu Cys

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Met His His His His His His Phe Pro Val Tyr Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide

<400> SEQUENCE: 14

Met His His His His His His Phe Pro Val Tyr Asp Tyr
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Met His His His His His His
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Phe Pro Val Tyr Asp Tyr Asp
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Pro Ala Ser Leu Lys Glu Ala Leu Ser Ala
1               5                   10

<210> SEQ ID NO 18
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 18

Ser Val Ala Lys Val Asn Ser Gln Ser Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Ser Pro Tyr Leu Phe Arg Ala Phe Arg Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ser Val Lys Arg Val Asn Ala Leu Asp Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Asp Ser Leu Thr Met Asp Leu Glu Phe Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Ile Gln Glu Thr Thr Cys Arg Arg Glu Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Glu Ala Asp Pro Ala Thr Cys Asp Phe Gln
1               5                   10

<210> SEQ ID NO 24
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 24

Arg Gly Tyr His Val Pro Val Ala Val Cys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Arg Ser Thr Val Arg Met Ser Ala Glu Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Val Gln Asn Val Trp Val Arg Cys His Trp
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

Ser Ser Ser Ser Gly Ser Ser Ser Ser Glu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide

<400> SEQUENCE: 28

Glu Met Phe Phe Gly Asp Ile Leu Gly Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide

<400> SEQUENCE: 29

Leu Thr Pro Asp Arg Ser Arg Gly Glu Pro
1               5                   10

<210> SEQ ID NO 30
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 30

Leu Tyr Glu Pro Ser Arg Glu Met Arg Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Asn Phe Pro Leu Gly Asn Arg Arg Tyr Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Asn Pro Trp Pro Arg Ala Arg Val Asn Pro
1               5                   10

<210> SEQ ID NO 33
<211> LENGTH: 600
<212> TYPE: DNA
<213> ORGANISM: Artificial Sequence
<220> FEATURE:
<223> OTHER INFORMATION: Synthetic SPP24

<400> SEQUENCE: 33
gcaagcttat cactcaaagc cagggtttac tcttgctctg ggccacgggt tcgagtacct      60
tctatttcca agaggaaagt ttcttctcat ctcacgtgat ggttcataaa gtggttcacc     120
tctggatctg tcaggagtga ggccaagcag gtaactgttt cttgatgtag aggatcccaa     180
gatatcccca aaaaacatct cttcactgct gctggaccca gagctggagg accagtggca     240
gcgaacccac acgttctgca cctgttcagc agacatccgc acggtgcttc tgcaaacggc     300
cacgggcacg tggtagcccc tctggaagtc acaggtggcg ggtctgcct cagattccct      360
cctgcacgtc gtctcttgaa tcctgaactc taagtccatg gtcaagctgt cctcgtccag     420
ggcgttgact cttttaactg agcttctaaa cgcccgaaac agatagggc tcagtgactg      480
ggaattcact tttgccacag aggcgctgag agcctccttc agggaagccg gtcatagtc     540
atacaccggg aagtggtggt ggtggtggtg catatgtata tctccttctt aaagttaaac     600

<210> SEQ ID NO 34
<211> LENGTH: 19
<212> TYPE: PRT
<213> ORGANISM: Artificial Sequence
<220> FEATURE:
<223> OTHER INFORMATION: Synthetic peptide

<400> SEQUENCE: 34

Cys Asp Ile His Val Leu Lys Gln Asp Gly Gln Phe Ser Val Leu Phe
1               5                   10                  15

Thr Lys Cys
```

```
<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Ser Thr Ser Arg Asn Ser Tyr Leu Leu Gly
1               5                   10
```

COMPOSITIONS COMPRISING SPP24 PEPTIDE FRAGMENTS

CROSS-REFERENCE TO RELATED APPLICATIONS

This application is a national stage entry of International Application No. PCT/US2011/037952 filed May 25, 2011, which in turn claims the benefit of U.S. Provisional Patent Application No. 61/348,205, filed May 25, 2010, the teaching of each of which is incorporated herein by reference in its entirety.

GOVERNMENT-SPONSORED RESEARCH AND DEVELOPMENT

This work was supported by the U.S. Department of Veterans Affairs, and the Federal Government has certain rights in the invention.

FIELD OF THE INVENTION

The present invention relates to a tumor suppression composition and methods of making and using the same.

BACKGROUND OF THE INVENTION

Secreted phosphoprotein-24 kDa (spp24) (UniProtKB, accession number: Q27967) is a glycoprotein that was first cloned from bovine bone matrix and subsequently found in the periosteum and liver, but not in the heart, lung, kidney, or spleen (Hu, B., et al., *J. Biol. Chem.*, 270, 431-436 (1995); Erratum (corrected accession number): *J. Biol. Chem.*, 270, 10359). It was later cloned in the mouse kidney (Okazaki, Y., et al., *Nature*, 420, 563-573 (2002)) and uterus (Strausberg, R., et al. *Proc. Natl. Acad. Sci. USA*, 99, 16899-16903 (2002)), rat liver, and human bone (Bennett, C. S., et al., *Matrix Biol.*, 22, 641-651 (2004)). Bovine spp24 is transcribed as a 203 amino acid residue protein. The first 23 residues constitute a signal peptide, which is cleaved to produce a mature 180 amino acid residue protein with a calculated mass of 20.5 kDa and a pI of 7.9 prior to modification. The N-terminal 107 amino acid residues of the mature protein constitute a cystatin or cysteine protease inhibitor domain, initially suggesting that one physiological role of spp24 might be to inhibit the cysteine proteases, such as cathepsin K, essential for bone resorption (Hu, 1995). Small amounts of spp24 were later found in the fetuin-mineral complex (FMC), a high molecular mass complex of calcium phosphate mineral, fetuin, and matrix Gla protein (MGP) initially discovered in the serum of etidronate-treated rats (Price, P. A., et al., *J. Biol. Chem.*, 278, 22153-22160 (2003)). Since the FMC is thought to play a critical role in inhibiting calcification of arteries and soft tissue in vivo, it was suggested that spp24, like fetuin and MGP, may inhibit calcification (Price, 2003). Alternatively, spp24, which contains a heavily phosphorylated serine-rich domain, may accumulate in bone and mineral complexes due to nonspecific ionic interactions with calcium (Hu, 1995).

Reported studies focus on the role of spp24 in the regulation of BMP bioactivity. While BMP is known to be an osteoinductive protein and can plan a role in tumor growth, functions and properties of spp24 with respect to tumor growth are otherwise largely unknown. Meanwhile, development of tumor such as cancer, particularly metastastic cancer, continues to pose major public health concerns, particularly among the aging population.

Therefore, there is a need for further development of anti-tumor compositions and methods.

The embodiments described below address the above-identified problems and needs.

For consistency, the gene (which is also known as SP2 or secreted phosphoprotein-2, vs. SP1 or osteopontin) is hereafter referred to as SPP24, while the protein containing 180 amino acid residues will be referred to as spp24 as noted in the original descriptions (Hu, 1995, Price, 2003), with amino acid residue numbers added as necessary for clarity.

SUMMARY OF THE INVENTION

In one aspect of the present invention, it is provided a composition. The composition comprises a bioactive agent in an effective amount that sequesters:

at least one bone morphogenetic protein (BMP) or a related protein, and at least one transforming growth factor-beta (TGF-β) family of cytokines, wherein the composition is effective for a disorder in a mammalian subject.

In some embodiments, the bioactive agent comprises secreted phosphorprotein 24 kD (spp24) (SEQ ID NO:1) (FIG. 2) or a fragment thereof, wherein the spp24 is in an effective amount for suppressing or delaying tumor growth.

In some embodiments, the spp24 is capable of sequestering one of bone morphogenetic protein-2 (BMP-2) and morphogenetic protein-7 (BMP-7) and as least one transforming growth factor-beta (TGF-β) family of cytokines so as to suppress or slow tumor growth in a mammalian subject.

The tumor can be any tumor. In some embodiments, the tumor is a metastatic cancer or a primary cancer. For example, the cancer can be metastatic or primary tumors selected from a tumor in bone, a lung tumor, a liver tumor, a brain tumor, a spinal tumor, a breast cancer, a prostate cancer, or any tumor type or individual tumor the growth of which is enhanced by growth factors of the TGF-beta family (e.g., a tumor that manifests with osteoblastic and/or bone metastases).

In some embodiments, the fragment of spp24 has a molecular weight from about 14 kD to about 20 kD.

The composition can be formulated in a formulation suitable for systemic or local delivery. In some embodiments, the formulation is a systemic delivery formulation. In some embodiments, the formulation is a local delivery formulation. Examples of local delivery formulation include, e.g., formulation for local injection or injection into a tumor, and a sustained release formulation. Examples of systemic delivery formulation can be, e.g., formulation for intravenous injection or subcutaneous injection. Examples of sustained release formulation can comprise, e.g., an implant or a patch to be administered at a site needing treatment.

In some embodiments, the composition can be a local delivery formulation comprising a patch suitable for delivery to the site of tumor.

In some embodiments, the composition of the various embodiments above can further comprise a pharmaceutically acceptable carrier.

In another aspect of the present invention, it is provided a method of treating or ameliorating a tumor, comprising administering to a patient a composition comprising spp24 or a fragment thereof, and wherein the spp24 is in an effective amount for suppressing or delaying tumor growth. In some embodiments, the spp24 is capable of sequestering one of bone morphogenetic protein-2 (BMP-2) and morphogenetic protein-7 (BMP-7) and possibly as least one transforming growth factor-beta (TGF-β) family of cytokines so as to suppress or slow tumor growth in a mammalian subject. In some other embodiments, the fragment of spp24 has a molecular weight from about 14 kD to about 20 kD. For example, the spp24 fragment can have amino acids 80-129.

In various embodiments of the above method, the composition can be formulated in a formulation suitable for systemic or local delivery. In some embodiments, the formulation is a systemic delivery formulation. In some embodiments, the formulation is a local delivery formulation. Examples of local delivery formulation include, e.g., formulation for local injection or injection into a tumor, and a sustained release formulation. Examples of systemic delivery formulation can be, e.g., formulation for intravenous injection or subcutaneous injection. Examples of sustained release formulation can comprise, e.g., an implant or a patch to be administered at a site needing treatment.

In some embodiments of the above method, the composition can be a local delivery formulation comprising a patch suitable for delivery to the site of tumor.

In some embodiments of the above method, the composition of the various embodiments above can further comprise a pharmaceutically acceptable carrier.

In another aspect of the present invention, it is provided a method of making a composition. The method comprises forming a composition of the various embodiments described above and below.

In a further aspect of the present invention, it is provided a method of producing recombinant spp24 or a fragment thereof. The method comprises expressing a gene comprises a nucleotide sequence encoding spp24 (SPP24) in an expression system. In some embodiments, the SPP24 comprises a nucleotide sequence selected from SEQ ID NO:2 (FIG. 2).

In some embodiments of the above method, the expression system comprises a mammalian cell, a plant cell, yeast, bacteria or is a cell-free expression system.

In some embodiments of the above method, the expression system comprises *E. coli*.

BRIEF DESCRIPTION OF THE DRAWINGS

FIG. 2 shows the sequence of the SPP24 insert (SEQ ID NOS: 1, 2, and 33) in SPP24/pET20b.

FIG. 7 shows cellular proliferation of A549 human non-small cell lung cancer cells after 48 hours of the indicated treatment with rhBMP-2, spp24, both rhBMP-2 and spp24, or vehicle alone.

FIG. 8 shows subcutaneous tumor formation eight weeks after injection of A549 human non-small cell lung cancer cells co-injected with rhBMP-2, spp24, both rhBMP-2 plus spp24 or vehicle alone.

DETAILED DESCRIPTION

Figure 1:
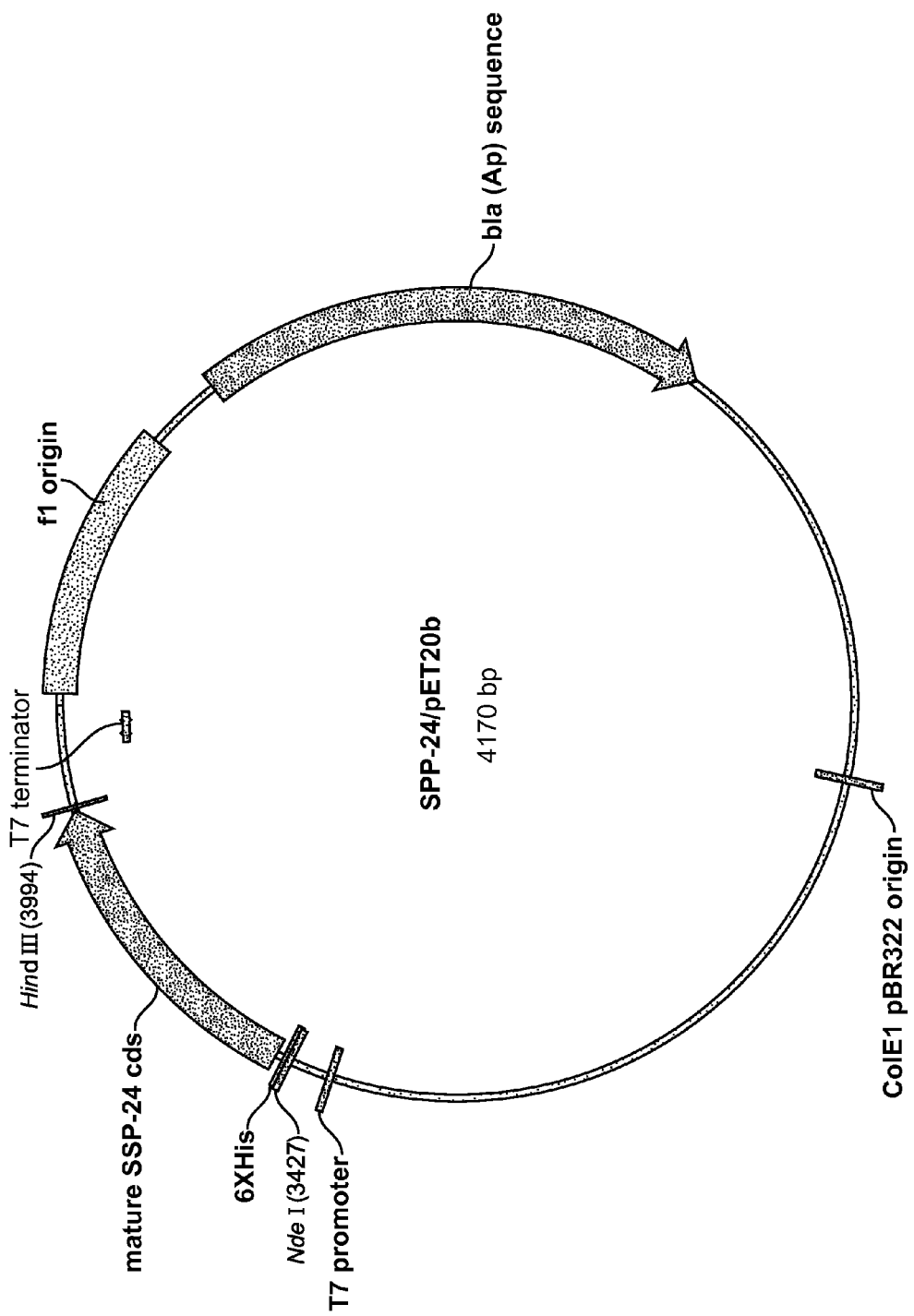
FIG. 1 shows the structure of SPP24/pET20b.

In one aspect of the present invention, it is provided a composition. The composition comprises a bioactive agent in an effective amount that sequesters:

at least one bone morphogenetic protein (BMP) or a related protein, and at least one transforming growth factor-beta (TGF-β) family of cytokines, wherein the composition is effective for a disorder in a mammalian subject.

In some embodiments, the bioactive agent comprises secreted phosphorprotein 24 kD (spp24) (SEQ ID NO:1) or a fragment thereof, wherein the spp24 is in an effective amount for suppressing or delaying tumor growth.

In some embodiments, the spp24 is capable of sequestering one of bone morphogenetic protein-2 (BMP-2) and morphogenetic protein-7 (BMP-7) and as least one transforming growth factor-beta (TGF-β) family of cytokines so as to suppress or slow tumor growth in a mammalian subject.

The tumor can be any tumor. In some embodiments, the tumor is a metastatic cancer or a primary cancer. For example, the cancer can be metastatic or primary tumor selected from a tumor in bone, a lung tumor, a liver tumor, a brain tumor, a spinal tumor, a breast cancer, or a prostate cancer. In some embodiments, the tumor can be any tumor type or individual tumor the growth of which is enhanced by growth factors of the TGF-beta family (e.g., a tumor that manifests with osteoblastic and/or bone metastases).

In some embodiments, the fragment of spp24 has a molecular weight from about 14 kD to about 20 kD. For example, the spp24 fragment can have amino acids 80-129.

The composition can be formulated in a formulation suitable for systemic or local delivery. In some embodiments, the formulation is a systemic delivery formulation. In some embodiments, the formulation is a local delivery formulation. Examples of local delivery formulation include, e.g., formulation for local injection or injection into a tumor, and a sustained release formulation. Examples of systemic delivery formulation can be, e.g., formulation for intravenous injection or subcutaneous injection. Examples of sustained release formulation can comprise, e.g., an implant or a patch to be administered at a site needing treatment.

In some embodiments, the composition can be a local delivery formulation comprising a patch suitable for delivery to the site of tumor.

In some embodiments, the composition of the various embodiments above can further comprise a pharmaceutically acceptable carrier.

In another aspect of the present invention, it is provided a method of treating or ameliorating a tumor, comprising administering to a patient a composition comprising spp24 or a fragment thereof, wherein the spp24 is in an effective amount for suppressing or delaying tumor growth. In some embodiments, the spp24 is capable of sequestering one of bone morphogenetic protein-2 (BMP-2) and morphogenetic protein-7 (BMP-7) and as least one transforming growth factor-beta (TGF-β) family of cytokines so as to suppress or slow tumor growth in a mammalian subject. In some other embodiments, the fragment of spp24 has a molecular weight from about 14 kD to about 20 kD.

In various embodiments of the above method, the composition can be formulated in a formulation suitable for systemic or local delivery. In some embodiments, the formulation is a systemic delivery formulation. In some embodiments, the formulation is a local delivery formulation. Examples of local delivery formulation include, e.g., formulation for local injection or injection into a tumor, and a sustained release formulation. Examples of systemic delivery formulation can be, e.g., formulation for intravenous injection or subcutaneous injection. Examples of sustained release formulation can comprise, e.g., an implant or a patch to be administered at a site needing treatment.

In some embodiments of the above method, the composition can be a local delivery formulation comprising a patch suitable for delivery to the site of tumor.

In some embodiments of the above method, the composition of the various embodiments above can further comprise a pharmaceutically acceptable carrier.

In another aspect of the present invention, it is provided a method of making a composition. The method comprises forming a composition of the various embodiments described above and below.

In a further aspect of the present invention, it is provided a method of producing recombinant secreted phosphorprotein 24 kD (spp24) or a fragment thereof. The method comprises expressing a gene comprises a nucleotide sequence encoding spp24 (SPP24) in an expression system. In some embodiments, the SPP24 comprises a nucleotide sequence of SEQ ID NO:2.

In some embodiments of the above method, the expression system comprises a mammalian cell, a plant cell, yeast, bacteria or is a cell-free expression system.

In some embodiments of the above method, the expression system comprises *E. coli*.

Spp24

Spp24 is documented to regulate bioactivities of BMP. The present invention discloses that the tumor suppression activities of spp24 are related to its ability to regulate BMP.

SPP24 maps to a region of the human genome associated with QTL linked to BUA (Wilson, 2004, Swallow, 1997, Bennett, 2004). Recently-published data confirm that spp24 and its derivatives are a new family of extracellular matrix phosphoproteins that contain a BMP-2-binding TRH1 or pseudoreceptor domain capable of modulating the rate and magnitude of bone formation (Behnam, K., et al., *J. Orthop. Res.*, 23, 175-180 (2005), Sintuu C, et al., J Orthop Res 2008; 26:753-758). Furthermore, the presence of promoters for GH and three differentiation- and development-related transcription factors (Bennett, 2004) that regulate mesenchymal cells suggests that SPP24 may be particularly important in early development and the acquisition of peak bone mass. SPP24 was not previously associated with the genetic regulation of bone mass, although Spp24 and its major degradation product (spp18.5) can be BMP-binding proteins because they share a common a TGF-beta receptor II homology-1 (TRH1) domain (Behnam, 2005). The synthetic, cyclic N- to C-terminally disulfide bonded peptide corresponding to the 19 amino acid residues of the TRH1 domain of spp18.5 and spp24 specifically binds recombinant human BMP-2 (rhBMP-2) and increases the rate and magnitude of BMP-2-mediated ectopic bone formation in vivo, when assessed histologically or densitometrically (Behnam, 2005). The 18.5 kDa pro-osteogenic protein identified as "BMP/NCP" by Urist, et al., (Urist, M., et al., Development and Diseases of Cartilage and Bone Matrix, pp. 149-176. (Alan R. Liss, New York) (1987)) was found to be a degradation product of the non-osteogenic parental protein, spp24 (Behnam, 2005).

Studies have found that Spp24 is a BMP-2-binding pseudoreceptor that modulates cytokine bioactivity and has significant effects on BMP-2-mediated bone formation in vivo. SPP24 (gene for secreted phosphoprotein-24 kDa; alternately known as secreted phosphoprotein-2 or SPP2) maps to chromosome 2q37.1 in the interval 233.64-233.67 Mb of the human genome (Swallow J E, et al., Cytogenet Cell Genet. 1997; 79:142; and Bennett C S, et al., Matrix Biol 2004; 22:641-51).

Ten SPP24 genes have been described, all of which are found in vertebrates (protein family [Pfam] PF07448) (Bennett, 2004). The spp24 proteins share 50% to 90% sequence identity, and consist of 3 major domains, including: (1) a short N-terminal secretory peptide, (2) a cystatin-(cysteine protease inhibitor)-like or cathelicidin-(neutrophil antimicrobial peptide precursor)-like domain with two internal disulfide bonds, and (3) a variable arginine-rich C-terminal region (Behnam, 2005, Hu, 1995).

The archetypical spp24 is bovine (b)-spp24, a 203 amino acid residue protein with a calculated mass of 23.1 kDa and a theoretical pI of 8.4 (Table 1) (ExPASY ProtParam). A signal peptide (residues 1-23) is cleaved, producing a mature protein of 180 residues (b-spp24, residues 24-203) with a calculated mass of 20.5 kDa and a pI prior to modification of 7.86 (Table 1).

Some of the research reports on spp24 are reviewed and summarized in Brochmann, E. J., et al., Metabolism; 58:644 (2009).

Tables 1 and 2 summarize some key information on amino acid sequence of domains of spp24 and related domain information.

TABLE 1

The amino acid sequence and structural domains of bovine spp-24, residues 1-203.*

MEKMAMKMLV$_{10}$ IFVLGMNHWT$_{20}$CTG↑FPVYDYD$_{30}$
PASLKEALSA$_{40}$;
(SEQ ID NO: 3)

SVAKVNSQSL$_{50}$SPYLFRAFRS$_{60}$SVKRVNALDE$_{70}$
DSLTMDLEFR$_{80}$;
(SEQ ID NO: 4)

IQETTCRRES$_{90}$EADPATCDFQ$_{100}$RGYHVPVAVC$_{110}$
RSTVRMSAEQ$_{120}$;
(SEQ ID NO: 5)

V$\underline{QNVWVRC}$HW$_{130}$SSSSGSSSSE$_{140}$EMF↑FGDILGS$_{150}$
STSRNSY↑LLG$_{160}$;
(SEQ ID NO: 6)

LTPDRSRGEP$_{170}$LYEPSREMRR$_{180}$NFPLGNRRYS$_{190}$
NPWPRARVNP$_{200}$GFE$_{203}$
(SEQ ID NO: 7)

Key Features:
1. Leader sequence: residues 1-23
2. Disulfide bonds: residues 86-97 and 110-128
3. Serine-rich domain: residues 131-139
4. TRH1 (TGF-β receptor II homology-1) domain ("BBP"): residues 110-128 (underlined)
5. Cystatin (cysteine protease inhibitor)- or cathelicidin-like domain: residues 24-130 (Italic)
6. "↑" indicates a labile cleavage site; spp24 is cleaved between residues 143 and 144 to form spp14.5, while cleavage between residues 157 and 158 produces spp16.
*Residue numbers are displayed as subscripts.

TABLE 2

The structure of the BMP-2-binding TRH1 domains of BBP/spp24, fetuin, and the TGF-β II receptor. The β-pleated sheets of fetuin and the TGF-β receptor II are underlined.

| Peptide or Protein: | Residue # | BMP-Binding TRH1 Sequence: | SSpro Secondary Structure Predicted*,** |
|---|---|---|---|
| BBP (the peptide) | 1-19 | CRSTVRMSAEQVQNVWVRC (SEQ ID NO: 8) | CCCEEEECHHHHEEEEEEC (SEQ ID NO: 9) |
| spp24 (the protein) | 110-128 | CRSTVRMSAEQVQNVWVRC (SEQ ID NO: 8) | CCCEEEECHHHHEEEEEEC (SEQ ID NO: 8) |
| Bovine fetuin-A | 114-132 | CDIHVL*KQDGQFSVLFTKC (SEQ ID NO: 9) | CCEEEEECCCCEEEEEECC (SEQ ID NO: 10) |
| Human TGF-β receptor II | 84-101 | C*VAVWRKNDENIT*LEYVC (SEQ ID NO: 11) | CEEEEECCCCCEEEEEEC (SEQ ID NO: 12) |

*H = alpha helix; E = β-pleated or extended strand; and C = the rest.
**http://www.igb.uci.edu/tools/scratch Fragments of spp24 can be made by recombinant genetic engineering methodology or by a hydrolysis process, e.g., proteolysis. Generally, recombinant fragments of spp24 can be made by expressing a gene encoding a spp24 fragment in an expression system. Expressing spp24 in an *E. coli* system is described below as an example.

As used in this invention, the term expression system can be a system cell free system or a system comprising a cell of an organism. Such an organism can be any living organism. Examples of such organisms are plant, yeast, bacteria (e.g., *E. coli*), an animal (e.g. a mammal), an insect, etc.

Dosages

Dosages of Spp24 or a fragment thereof can be determined according to methods known in the art based on type of agent, the disease, and other factors such as age and gender. Generally, dosages can vary according to the types of agent (spp24 or a fragment thereof), type of disease or disorder (e.g., a tumor, type of tumor, etc), as well age and gender.

In one embodiment, the dosage of Spp24 or a fragment thereof for tumor is generally in the milligram quantities, e.g., ranging from about 1 mg to about 500 mg, for topical administration. For administration by injection (subcutaneous injection of IV) for a 70 kg adult human, the doses can be, e.g., 1 mg, or a dose from 10 µg to about 10 mg.

Furthermore, it is understood that all dosages may be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Formulation Carriers

The pharmaceutical composition described herein may be administered to a subject in need of treatment by a variety of routes of administration, including orally and parenterally, (e.g., intravenously, subcutaneously or intramedullary), intranasally, as a suppository or using a "flash" formulation, i.e., allowing the medication to dissolve in the mouth without the need to use water, topically, intradermally, subcutaneously and/or administration via mucosal routes in liquid or solid form. The pharmaceutical composition can be formulated into a variety of dosage forms, e.g., extract, pills, tablets, microparticles, capsules, oral liquid.

There may also be included as part of the pharmaceutical composition pharmaceutically compatible binding agents, and/or adjuvant materials. The active materials can also be mixed with other active materials including antibiotics, antifungals, other virucidals and immunostimulants which do not impair the desired action and/or supplement the desired action.

In some embodiments, the composition can be formulated into a formulation for bone, which can include a carrier such as collagen, atelocollagen (collagen treated to remove the immunogenic ends), hydroxyapatite, and a polymer, which is further described below. In these embodiments, the formulation can comprise a porous matrix or microspheres made of a polymeric material, which is further described below. In some embodiments, the polymer can be, e.g., polylactic acid or polylactide (PLA), or poly(lactic acid-co-glycolic acid), or another bioabsorbable polymer.

In one embodiment, the mode of administration of the pharmaceutical composition described herein is oral. Oral compositions generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. Some variation in dosage will necessarily occur, however, depending on the condition of the subject being treated. These preparations should produce a serum concentration of active ingredient of from about 0.01 nM to 1,000,000 nM, e.g., from about 0.2 to 40 µM. A preferred concentration range is from 0.2 to 20 µM and most preferably about 1 to 10 µM. However, the concentration of active ingredient in the drug composition itself depends on bioavailability of the drug and other factors known to those of skill in the art.

In another embodiment, the mode of administration of the pharmaceutical compositions described herein is topical or mucosal administration. A specifically preferred mode of mucosal administration is administration via female genital tract. Another preferred mode of mucosal administration is rectal administration.

Various polymeric and/or non-polymeric materials can be used as adjuvants for enhancing mucoadhesiveness of the pharmaceutical composition disclosed herein. The polymeric material suitable as adjuvants can be natural or synthetic polymers. Representative natural polymers include, for example, starch, chitosan, collagen, sugar, gelatin, pectin, alginate, karya gum, methylcellulose, carboxymethylcellulose, methylethylcellulose, and hydroxypropylcellulose. Representative synthetic polymers include, for example, poly (acrylic acid), tragacanth, poly(methyl vinylether-co-maleic anhydride), poly(ethylene oxide), carbopol, poly(vinyl pyrrolidine), poly(ethylene glycol), poly(vinyl alcohol), poly (hydroxyethylmethylacrylate), and polycarbophil. Other bioadhesive materials available in the art of drug formulation can also be used (see, for example, Bioadhesion—Possibilities and Future Trends, Gurny and Junginger, eds., 1990).

It is to be noted that dosage values also varies with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The formulation may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The pharmaceutical compositions of the present invention are prepared as formulations with pharmaceutically acceptable carriers. Preferred are those carriers that will protect the active compound against rapid elimination from the body, such as a controlled release formulation, including implants and microencapsulated delivery systems. Biodegradable, biocompatable polymers can be used, such as polyanhydrides, polyglycolic acid, collagen, and polylactic acid. Methods for preparation of such formulations can be readily performed by one skilled in the art.

Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Joni, G.; Bertoloni, G.; Milanesi, C.; Sicuro, T. Chem. Biol. Interact. 53, 131-143 (1985) and by Jori, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Joni, G.; Reddi, E.; Cozzani, I.; Tomio, L. Br. J. Cancer, 53(5), 615-21 (1986).

The pharmaceutical composition described herein may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like according to a specific dosage form.

Thus, for example, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

The pharmaceutical composition described herein can be formulated alone or together with the other agent in a single dosage form or in a separate dosage form. Methods of preparing various pharmaceutical formulations with a certain amount of active ingredient are known, or will be apparent in light of this disclosure, to those skilled in this art. For examples of methods of preparing pharmaceutical formulations, see Remington's Pharmaceutical Sciences, Mack Publishing Company, Easton, Pa., 19th Edition (1995).

In some embodiments, the composition of the various embodiments disclosed above can be formulated into implants, scaffolds, patches, etc.

Use of the Composition

In accordance with embodiments of the invention, a pharmaceutical composition of the various described embodiments can be administered to a mammal for treating or preventing a tumor. As used herein, the term "mammal" encompasses all mammalian subjects including human beings and animals.

The tumor can be any tumor. In some embodiments, the tumor is a metastatic cancer or a primary cancer. For example, the cancer can be metastatic or primary tumors selected from a tumor in bone, a lung tumor, a liver tumor, a brain tumor, a spinal tumor, a breast cancer, a prostate cancer, or any tumor type or individual tumor the growth of which is enhanced by growth factors of the TGF-beta family (e.g, a tumor that manifests with osteoblastic and/or bone metastases).

The various bone conditions that can be treated, prevented, and/or ameliorated by the pharmaceutical composition described herein are described above.

EXAMPLES

The embodiments of the present invention will be illustrated by the following set forth examples. All parameters and data are not to be construed to unduly limit the scope of the embodiments of the invention.

Example 1

Studies on Recombinant Expression, Isolation, and Proteolysis of Extracellular Matrix Secreted Phosphoprotein-24 kDa Summary Secreted phosphoprotein-24 kDa (spp24) is an extracellular matrix protein first cloned from bone. Bovine spp24 is transcribed as a 203 amino acid residue protein that undergoes cleavage of a secretory peptide to form the mature protein (spp24, residues 24 to 203). While not osteogenic itself, spp24 is degraded to a possibly somewhat osteogenic protein, spp18.5, in bone. Both spp18.5 and spp24 contain a cyclic TRH1 (TGF-beta receptor II homology-1) domain similar to that found in the receptor itself and in fetuin. A synthetic peptide including 19 amino acids, which is cyclic and derived from the sequence of the bovine protein, called Bone Morphogenetic Protein Binding Peptide or BBP, aka cbBBP (cyclic, bovine BBP), corresponding to the TRH1 domain of spp18.5 and spp24, specifically binds BMP-2 and enhances the rate and magnitude of BMP-2-induced ectopic bone formation in vivo. The parental protein, spp24, exhibits a high affinity for bone and mineral complexes, but its abundance there is low, suggesting that it is rapidly degraded. The availability of recombinant spp24 and its degradation products would facilitate the elucidation of their structure: function relationships. We now describe the expression of $His_6$-tagged bovine spp24 (residues 24 to 203) (SEQ ID NO:1) (FIG. 2) in *E. coli*, its purification by high-resolution IMAC (immobilized metal affinity chromatography), and the characterization of the full-length recombinant 21.5 kDa protein and its two major 16 kDa and 14.5 kDa degradation products (spp24, residues 24 to 157, and spp24, residues 24 to 143) by mass spectroscopy. The recombinant spp24 protein was resistant to proteolysis by MC3T3-E1 osteoblastic cell extracts in the absence of calcium; however, in the presence of 4 mM Ca, it can undergo essentially complete proteolysis to small peptides, by-passing the 16 kDa and 14.5 kDa intermediates. This confirms the proteolytic susceptibility of spp24. It also suggests that the levels of spp24 in bone may be regulated, in part, by calcium-dependent proteolysis mediated by osteoblastic cells.

We now describe a method for producing spp24, residues 24 to 203, in *E. coli*, isolating it in bulk by affinity chromatography, and characterizing the proteolytic susceptibility of the product.

Materials and Methods

Materials

The pET20b expression system, *E. coli* BL21(DE3) host strain, media, antibiotics, protein extraction reagents, lysozyme, His-Tag monoclonal antibody, and Western blotting reagents were from Novagen (EMD Biosciences, La Jolla, Calif.). Protein assay kits and electrophoresis supplies, including precast 4% to 20% polyacrylamide gradient minigels, were from Pierce Chemical Company (Rockford, Ill.). $His_6$-protease inhibitor (containing [4-(2-aminoethyl)benzenesulfonyl fluoride HCl] or AEBSF, bestatin HCl, [N-(trans-epoxysuccinyl)-L-leucine 4-guanidinobutylamide] or E64, pepstatin A, and disodium phosphoramidon), salts and buffers were from Sigma Chemical Company (St. Louis, Mo.). HiTrap IMAC Fast Flow Sepharose 6 columns were from GE Healthcare (Uppsala, Sweden). Affinity-purified rabbit anti-bovine spp24 (residues 168 to 180) was obtained from Genemed (San Francisco, Calif.).

Expression of spp24 in *E. coli*

SPP24 (SEQ ID NO:2) was commercially cloned from a bovine liver cDNA library by RT-PCR of SPP24-specific primers. The complete nucleotide sequence for the mature, secreted isoform of bovine spp24 (corresponding to amino acid residues 24 to 203) plus an N-terminal Met-$(His)_6$ extension was cloned into a vector (pcDNA3.1/V5-H isA; Invitrogen, Carlsbad, Calif.). The entire plasmid sequence was confirmed by DNA sequencing (Genedynamics, Portland, Oreg.). The coding sequence was amplified from the plasmid 24 kD/pcDNA3.1/V5-His A using a 5'NdeI-HIS primer and a 3'-HindIII primer, and inserted into the pET20b vector according to the manufacturer's instructions (EMD Biosciences, La Jolla, Calif.). The HIS-SPP24 coding region was sequence-verified on two strands. The plasmid was transformed into *E. coli* cell line BL21(DE3) and maintained as a bacterial stab culture in 100 μg/ml ampicillin.

Expression and Purification of $His_6$-Tagged spp24

Transfected *E. coli* were seeded onto imMedia Amp Agar (Invitrogen, Carlsbad, Calif.). Single colonies were cultured in 50 ml of imMedia Liquid Amp, grown for 4 to 6 hr at 37° C. with orbital shaking (120 rpm), pelleted by low-speed centrifugation at room temperature, resuspended in 50 ml of fresh imMedia Liquid Amp plus carbenicillin (50 μg/ml), and cultured for 3 to 4 hr. This inoculum was added to 1 liter of Overnight Express Instant TB Medium plus 1% glycerol. The cells were cultured to stationary phase in a shaking water bath at 37° C. for 16 hr. Preliminary fractionation and Western blotting experiments indicated that spp24 was present in the inclusion bodies, but not in the media or periplasmic space (data not shown). Inclusion bodies were prepared and solubilized using BugBuster protein extraction reagents as outlined by the manufacturer (Novagen, La Jolla, Calif.) with the addition of $His_6$ protease inhibitor cocktail (Sigma, St. Louis, Mo.) at all steps. Briefly, the cells were pelleted by centrifugation at 10,000×g for 10 min at 4° C. in a Sorval GSA rotor. The supernatant was discarded, and the wet mass of the cell pellets was determined gravimetrically. The wet pellets were resuspended in 5 ml of BugBuster protein extraction reagent and 20 μl of lysonase per gram of wet pellet weight (initial suspension volume) plus 1% (v/v) $His_6$ protease inhibitor cocktail. The cell suspension was incubated with shaking (120 rpm) at room temperature for 20 min. The extract was centrifuged at 4° C. for 20 min at 16,000×g in a Sorval SS-34 rotor. The supernatant was discarded, and the pellet was resuspended in the same volume of BugBuster protein extraction reagent and protease inhibitor cocktail. A 6-fold volume of 0.1× BugBuster and protease inhibitor cocktail was added with vortexing for 1 min. The suspension was centrifuged at 5,000×g for 15 min at 4° C. in a Sorval GSA rotor. The supernatant was discarded. The pellet was resuspended in half of the initial suspension volume of 0.1× BugBuster and $His_6$ protease inhibitor cocktail, mixed by vortexing, and centrifuged for 15 min at 5,000×g in a Sorval SS-34 rotor at 4° C. The pellet was resuspended in 0.1× BugBuster plus protease inhibitor cocktail, vortexed, and centrifuged for 15 min at 10,000×g in a Sorval SS-34 rotor at 4° C. The supernatant was discarded, and the pellet containing the inclusion bodies was subjected to IMAC, as described in detail below.

$His_6$-tagged spp24 was isolated from inclusion bodies by immobilized metal affinity chromatography (IMAC) on HiTrap IMAC FF columns (GE Healthcare Amersham Biosciences, Uppsala, Sweden) using a BioLogic protein purification workstation (BioRad, Hercules, Calif.). The column bed volume was 1.0 ml, and the flow rate was 1.0 ml/min. Prior to use, the columns were washed with 10 ml of distilled water to remove residual ethanol, charged with 0.5 ml of 100 mM cobalt chloride in distilled water, washed with 5 ml of distilled water, and pre-equilibrated with 10 ml of filtered, degassed Buffer A (8 M deionized urea, 100 mM sodium phosphate buffer [pH 7.4], 20 mM imidazole). The inclusion body pellet derived from 1 liter of cells was suspended in 5 ml of buffer A, transferred to 1.7-ml microcentrifuge tubes, centrifuged at maximum speed (14,000 rpm) in a Beckman model 5415C microfuge for 2 min to pellet insoluble material, then applied to a loading loop. The fraction size was 1.0 ml. The column was pre-equilibrated with 5 ml of buffer A to achieve a stable baseline, and the sample was loaded onto the column through a 1.0-ml static loop. Multiple injections were required to load sample volumes >1.0 ml. The unbound proteins were isocratically eluted with 10 ml of Buffer A. Bound proteins were eluted with a 10 ml linear gradient of 0% to 100% buffer B (8 M urea, 100 mM sodium phosphate [pH 7.4], 500 mM imidazole), followed by 10 ml of 100% buffer B. A 3-ml linear gradient from 100% to 0% buffer B, and 10 ml of isocratic flow at 100% buffer A were used to return the column to baseline conditions.

Molecular Weight Determinations

The proteins in representative 1-ml IMAC fractions containing $His_6$-spp24 and its degradation products were passed through a C18 reverse phase tip to desalt them, then subjected to high-resolution MS to determine their precise molecular weights on a fee-for-service basis (Mary Ann Gawinowicz, Ph.D., Protein Chemistry Core Facility, Howard Hughes Medical Institute, Columbia University, New York, N.Y.).

Electrophoresis and Western Blotting

1D SDS 4% to 20% polyacrylamide gradient gel electrophoresis, Coomassie Brilliant Blue staining of gels, protein transblotting and Western development were conducted using standard equipment and commercial reagents as previously outlined in detail (Behnam, 2005, Behnam, K., et al., *Connective Tissue Res.*, 47, 271-277 (2006); Behnam, K., et al., *J. Orthop. Res.*, 20, 1190-1196 (2002); and Behnam, K., Murray, S. S., et al., *J. Orthop. Res.*, 23, 618-624 (2005)). Visualization of $His_6$-tagged spp24 was accomplished by Western blotting using a primary antibody and colorimetric kit from Novagen (EMD Biosciences, La Jolla, Calif.). Visualization of the C-terminal domain of bovine spp24 (residues 168 to 180) was accomplished by Western blotting using an affinity-purified rabbit antibody to the keyhole limpet-conjugated peptide and a kit from Vector Laboratories (Burlingame, Calif.). The primary antibodies (mouse monoclonal anti-His.Tag and rabbit anti-bovine spp24 [residues 168 to 180]) were used at a final concentration of 1 μg/ml. The secondary antibody directed against the mouse monoclonal anti-His.Tag was goat anti-mouse IgG conjugated to alkaline phosphatase, and it was used at a 1:5000 dilution. The secondary antibody directed against the rabbit anti-bovine spp24 (residues 168 to 180) was donkey anti-rabbit IgG conjugated to alkaline phosphatase, and it was used at a 1:2500 dilution. Color development was accomplished with BCIP/NBT in alkaline buffer.

2D SDS-PAGE, MALDI/ToF MS, and N-Terminal Sequencing:

The proteins in representative fractions containing $His_6$-spp24 and its degradation products were separated by 2D SDS-PAGE by the method of O'Farrell (O'Farrell P. H., *J. Biol. Chem.*, 250, 4007-4021 (1975)) (Nancy Kendrick, Ph.D., Kendrick Laboratories, Madison, Wis.) (Behnam, 2005, Behnam, 2006; Behnam, 2002; and Behnam and Murray, 2005). These fractions had been stored at −20° C. for 3 months in urea buffer plus protease inhibitors, resulting in the slow accumulation of degradation products similar to those previously reported (Urist, 1987) that are not abundant in freshly-prepared fractions. The gel was stained with Coomassie Brilliant Blue, and the three major spots of the appropriate molecular weight (<24 kDa) were selected, excised, eluted, reduced in 5% β-mercaptoethanol, alkylated, trypsin digested, and subjected to peptide mass fingerprint analysis by MALDI/ToF MS (Mary Ann Gawinowicz, Ph.D., Protein Chemistry Core Facility, Howard Hughes Medical Institute, Columbia University, New York, N.Y.) to verify their identities and structures (Behnam, 2005, Behnam, 2006, Behnam, 2002; and Behnam and Murray, 2005). Methionines were not oxidized. Peptides with a mass $[M+H^+]>1000$ Da were analyzed. The peptide fingerprint was compared to those in the SWISS-PRO and NCBI databanks (Behnam, 2005, Behnam, 2006; Behnam, 2002; and Behnam and Murray, 2005). The spots in replicate gels were subjected to N-terminal sequencing by automated Edman degradation. 2D gels were used for these analyses because the resolution of closely-related proteins is greater, permitting easier identification, excision, and post-electrophoresis characterization, such as N-terminal sequencing.

Proteolytic Susceptibility of spp24 (Residues 23 to 204)

MC3T3-E1 mouse preosteoblastic cells were cultured to confluence, harvested by trypsinization, pelleted by centrifugation, and suspended in digestion buffer (100 mM HEPES-HCl, pH 7.5, 12.5 mM KCl, 6.25 mM (3-mercaptoethanol, and 0.2% Triton X-100) plus or minus 4 mM $CaCl_2$ at a protein concentration of 2.4 mg/ml. Recombinant spp24 (residues 23 to 204) was exhaustively dialyzed vs. water, lyophilized, and resuspended at 1 mg/ml in digestion buffer (plus or minus 4 mM $CaCl_2$). Equal volumes of cell extract and spp24 were combined, and incubated at 37° C. for 0 to 24 hours. At the intervals indicated, 4 μl aliquots equivalent to 2 μg spp24 were removed, subjected to SDS-PAGE, and Western blotted using antibody directed against the $His_6$ tag as outlined in detail above.

Results

Figure 3:
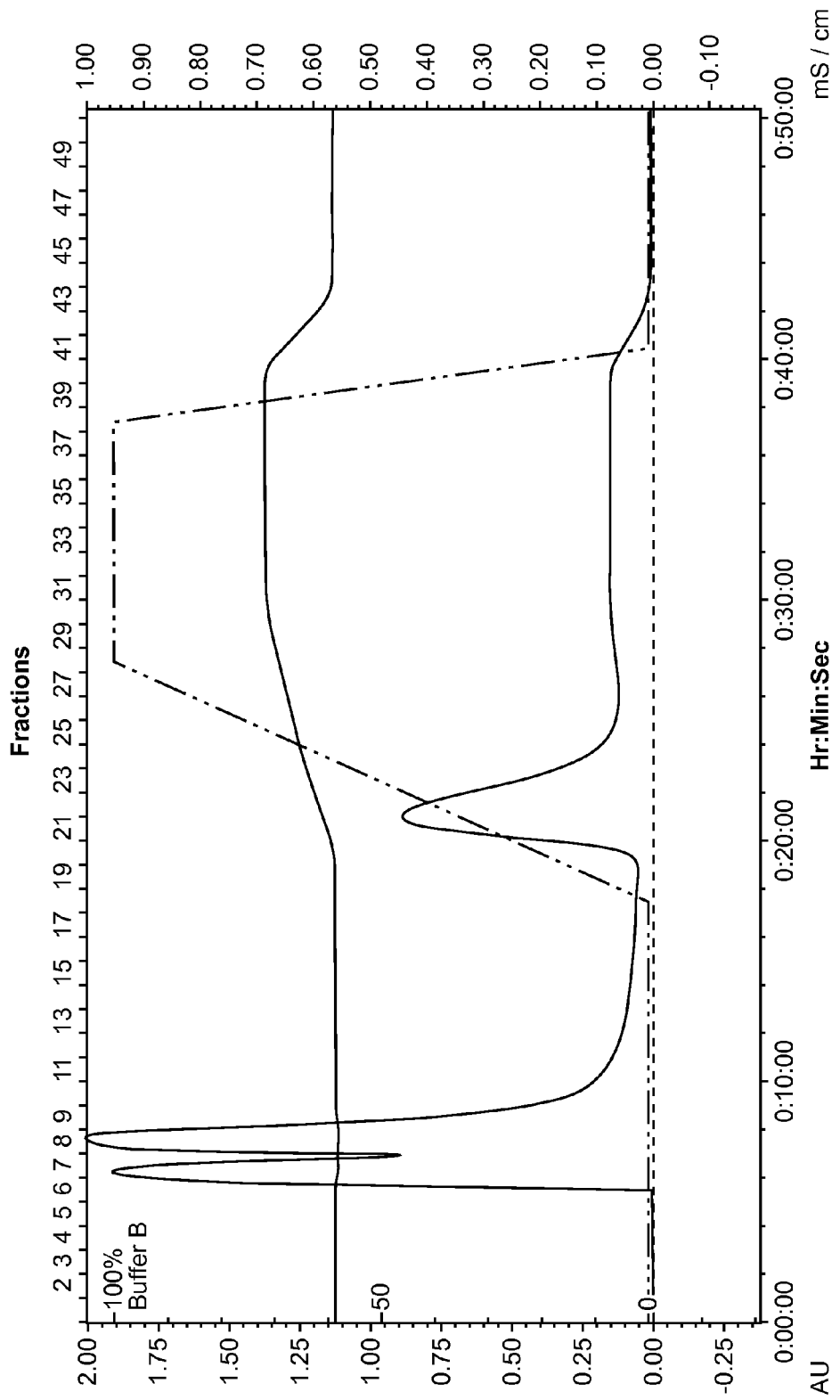
FIG. 3 shows the chromatogram showing fractionation of unbound inclusion body protein (Fractions 6-9) and $His_6$-tagged spp24 (Fractions 19-23) by FF IMAC chromatography.
Figure 4:
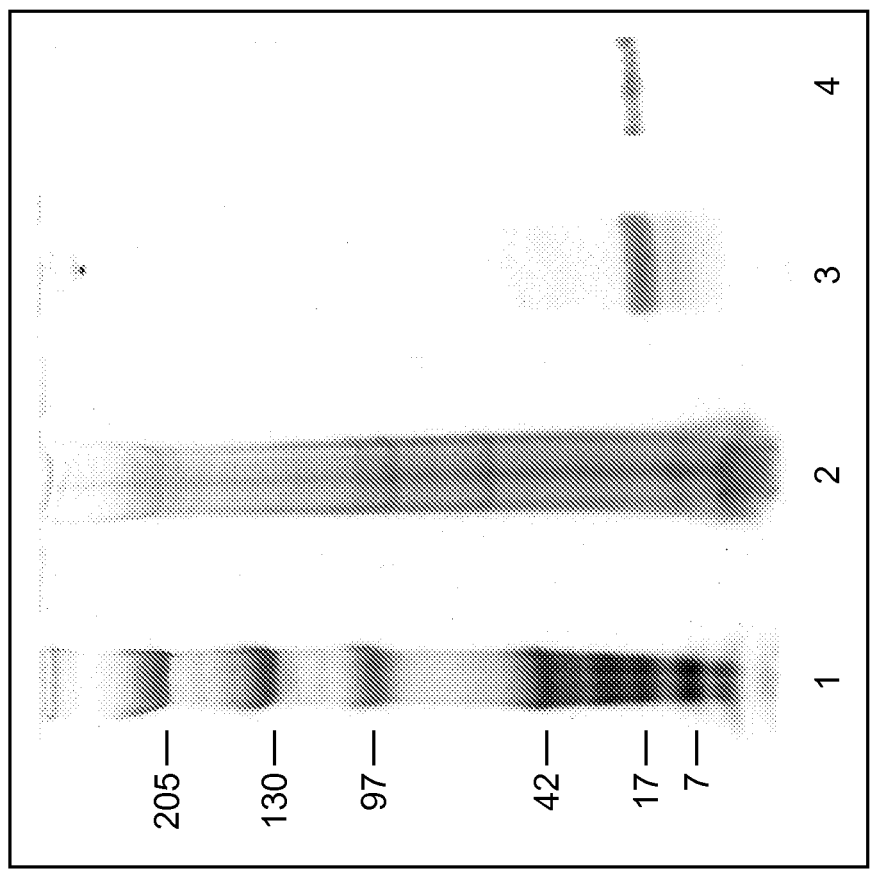
FIG. 4 shows Coomassie-blue stained 4% to 20% polyacrylamide gradient gels and Western blots showing proteins in freshly-prepared IMAC column fractions. Lane 1: Molecular weight standards. Lane 2: Unbound proteins (100 μg of pooled fractions 6-9).
Figure 5:
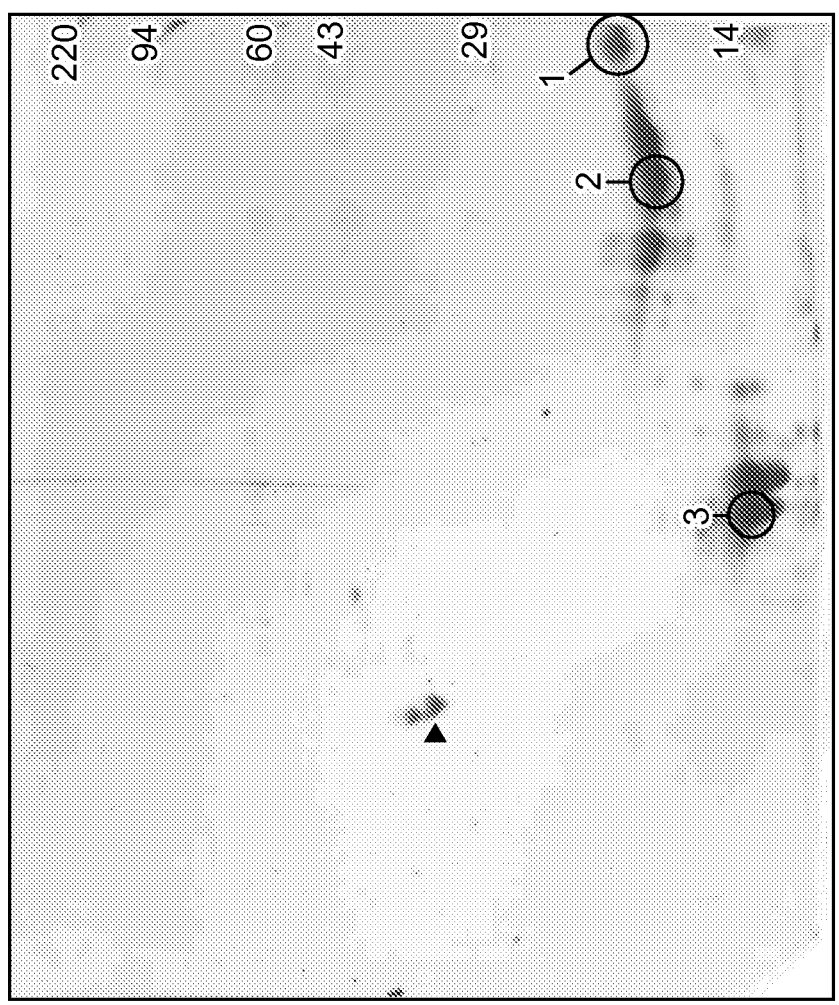
FIG. 5 shows Coomassie Brilliant Blue R250-stained 2D SDS-PAGE of proteins in IMAC-bound fractions stored at −20° C. for 3 months.

The map of the HIS-SPP24 pET20B expression vector is shown in FIG. 1. DNA sequencing confirmed that it corresponds to a construct with an N-terminal Met followed by a $His_6$-tag, and residues 24 through 203 of bovine spp24 (FIG. 2). When plasmid expression was induced in the host E. coli strain [BL21(DE3)], the recombinant protein appeared in significant amounts in the inclusion bodies, as illustrated by the cobalt-binding peak in fractions 19 through 24 in the chromatogram (FIG. 3). Unbound proteins eluted in Fractions 6 to 8. The apparent doublet represents flow through of unbound proteins following two injections of solubilized inclusion body proteins through a 1.0-ml static injection loop, with a brief pause between injections. The $His_6$-tagged spp24 proteins eluted as a single peak starting at 19% Buffer B (100 mM imidazole). The yield was 5 to 8 mg $His_6$-spp24 per liter of cultured bacteria. Freshly IMAC-purified fractions of spp24 contained a single major protein band at about 21 kDa on 1D SDS 4% to 20% polyacrylamide gradient gels (FIG. 4, Lane 3) that was confirmed to be $His_6$-spp24 by Western blotting (FIG. 4, Lane 4). The 21 kDa protein is highly susceptible to proteolysis, even when stored frozen in 8 M urea in the presence of protease inhibitors. For example, 2D SDS-PAGE gels of IMAC-purified $His_6$-spp24 that had been frozen at −20° C. for 3 months showed a much more complex pattern of proteins (FIG. 5) than the one that was observed on 1D gels of freshly-purified protein (FIG. 4). 2D SDS-PAGE resolved at least 3 major groups of proteins that ranged in apparent mass from about 21 kDa (Spot 1) to about 14 kDa (a major doublet including Spot 3), with a series of overlapping protein spots of intermediate mass of around 16 kDa (includes Spot 2) (FIG. 5). All of the major spots shown on the Coomassie blue-stained 2D gel (FIG. 5) were similarly positively immunostained with a commercial mouse monoclonal antibody directed against the N-terminal $His_6$ tag, indicating the presence of the intact N-terminal (data not shown). Spots 2 and 3 were excised, and their N-terminal sequences were confirmed to be M(H)$_6$FPVYD (SEQ ID NO:13) and M(H)$_6$FPVYDY (SEQ ID NO:14), respectively, by Edman degradation. When 2D transblots were immunoblotted with a rabbit polyclonal antibody that recognized the more C-terminal epitope of bovine spp24 (residues 168 to 180), Spot 1 was as intensely immunostained as it had been when probed with the antibody to the N-terminal (His)$_6$ epitope, while lower-molecular weight spots were not (data not shown). This suggested that the C-terminus of the recombinant protein is labile to proteolysis, as predicted for the native protein by Hu, et al. (Hu, 1995). Mass spectroscopy of the total mixture of proteins in the IMAC-bound fractions was used to resolve Met(His)$_6$-spp24 (residues 24 to 203) from its C-terminally truncated daughter proteins, and the results are shown in Table 3. The full-length protein with a calculated molecular weight of 21,435 Da [Met(His)$_6$-spp24 (residues 24 to 203)] and two major degradation products with calculated molecular weights of 16,000 Da [Met(His)$_6$-spp24 (residues 23 to 157)] and 14,511 Da [Met(His)$_6$-spp24 (residues 23 to 143)] were present the IMAC-bound fractions. Their identification as spp24 degradation products was verified by MALDI-ToF MS (Behnam, 2005) (data not shown). All of these proteins exhibited some degree of carbamoylation (condensation of a primary amine group, probably the N-terminus, with cyanate ions derived from urea degradation), which resulted in complex spectra. Where multiple peaks corresponding to both the noncarbamoylated and carbamoylated proteins could not be resolved, the centroided mass for both is listed (Table 3). About 30% of the full-length protein, 45% of Met(His)$_6$-spp24 (residues 23 to 157), and 80% of Met(His)$_6$-spp24 (residues 23 to 143) were typically estimated to be carbamoylated (Mary Ann Gawinowicz, personal communication).

FIG. 3 shows the chromatogram showing fractionation of unbound inclusion body protein (Fractions 6-9) and $His_6$-tagged spp24 (Fractions 19-23) by FF IMAC chromatography. The IMAC column was initially charged with cobalt. Blue line: UV absorbance (AU); Red line: Conductivity (mS/cm); Black line: % B. Buffer A: 8 M urea, 100 mM sodium phosphate buffer [pH 7.4], 20 mM imidazole; Buffer B: Buffer A+100 mM imidazole.

FIG. 4 shows Coomassie-blue stained 4% to 20% polyacrylamide gradient gels and Western blots showing proteins in freshly-prepared IMAC column fractions. Lane 1: Molecular weight standards. Lane 2: Unbound proteins (100 μg of pooled fractions 6-9). Lane 3: 5 μg of dialyzed spp24 (pooled bound fractions). Lane 4: Western blot of proteins in Lane 3 showing immunopositive $His_6$-spp24 bands in IMAC fractions. Note that a single major band at 21 kDa is observed in this freshly-prepared preparation of spp-24.

FIG. 5 shows Coomassie Brilliant Blue R250-stained 2D SDS-PAGE of proteins in IMAC-bound fractions stored at −20° C. for 3 months. Molecular weight markers appear on the right margin; the internal pI standard (33 kDa tropomyosin, pI=5.2) is indicated with an arrow. Three major sets of spots containing recombinant Met(His)6-spp24 (residues 24 to 203)-derived proteins are present. Spots 2 and 3 were excised and subjected to N-terminal degradation and MS fingerprinting and confirmed to be derived from Met(His)$_6$-spp24.

Figure 6:
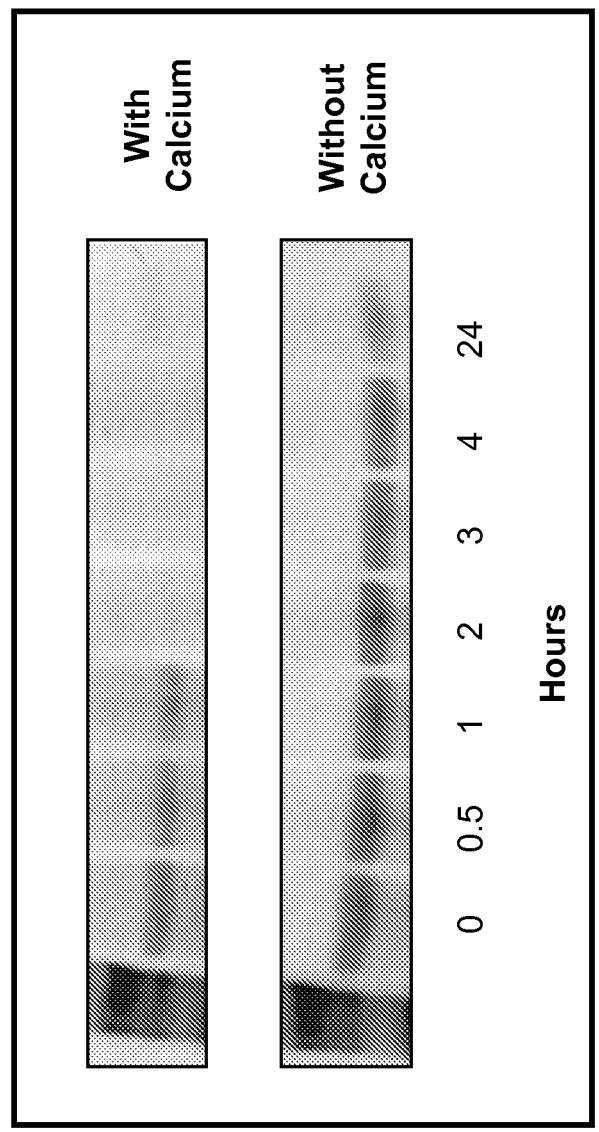
FIG. 6 shows the results of proteolysis of Met$(His)_6$-spp24 (residues 24 to 203) by MC3T3-E1 cell extracts.

Freshly-isolated $His_6$-spp24 was incubated with extracts of confluent mouse MC3T3-E1 osteoblastic cells in the absence and presence of 4 mM total calcium. In the absence of added calcium, essentially no degradation was observed until 24 hr of incubation (FIG. 6). However, in the presence of calcium, essentially complete degradation of $His_6$-spp24 was observed in about 2 hours (FIG. 6), confirming the susceptibility of the protein to proteolysis. The proteolysis observed in the presence of calcium differs from the proteolysis observed during long-term storage of $His_6$-spp24. In the presence of calcium, spp24 is rapidly degraded to small peptides (<7 kDa) (FIG. 6), while long-term storage in the absence of calcium is associated with the gradual appearance of two proteins (spp14.5 and spp16) of intermediate size (FIG. 5).

FIG. 6 shows the results of proteolysis of Met(His)$_6$-spp24 (residues 24 to 203) by MC3T3-E1 cell extracts. The recombinant protein was incubated with solubilized cell extracts in the absence or presence of 4 mM calcium for up to 24 hr. Aliquots corresponding to 2 μg of spp24 were removed, subjected to SDS-PAGE, and Western blotted with anti-His$_6$ as outlined in the text. In the presence of calcium, essentially all of the spp24 is degraded within about 2 hours. No accumulation of proteins with intermediate molecular weights of 14.5 kDa and 16 kD is observed in the presence of calcium.

Discussion

Secreted phosphoprotein-24 kDa is a relatively rare extracellular matrix protein (Hu, 1995, Behnam, 2005, Urist, 1987). The highest levels of the intact 24 kDa protein and its major degradation product (spp18.5) are observed in bone mineral (Hu, 1995, Urist, 1987). Although trace amounts of spp24 are also present in fetuin-mineral complexes (Price, 2003), and spp24 transcripts are expressed in a variety of other vertebrate mesodermal tissues (Okazaki, 2002; Strausberg, 2002; and Bennett, 2004), its functions remain poorly characterized. The insolubility, low abundance, and susceptibility to proteolysis of spp24 made it difficult to isolate and characterize by classical biochemical approaches (Hu, 1995, Behnam, 2005). In order to overcome these difficulties, we have expressed the secreted isoform of bovine spp-24 (residues 24 to 203) in *E. coli*. A penultimate N-terminus (His)$_6$ tag affinity tag was added to facilitate isolation, while an N-terminal Met residue was added to improve protein stability. A simple method for the rapid isolation of milligram quantities of the protein from inclusion bodies by IMAC affinity chromatography in urea buffer was developed, after empirically determining that charging the column with cobalt, rather than nickel, gave the lowest back pressure, longest column life, and most consistent elutions (data not shown). Previous research has demonstrated that spp18.5 is the protein identified as "BMP/NCP" (Behnam, 2005) by Urist, et al. (Urist 1987; Urist, M. R., et al., *Proc. Natl. Acad. Sci. USA*, 81, 371-375 (1984)), who were probably unable to N-terminally sequence the protein and identify it because the N-terminus was blocked. Carbamoylation of "BMP/NCP" by cyanate ions (a degradation product of urea) may account for the N-terminal blockage of the native protein isolated from bone, as well as the complex MS profiles observed in recombinant Met(His)$_6$-spp24 (residues 24-203) and its 16 kDa and 14.5 kDa degradation products (Table 3). The 8 M urea used in the buffers described was deionized prior to use to remove cyanate ions, but this did not prevent carbamoylation.

Spp24 contains two major functional domains, including a cystatin (cysteine-protease inhibitor) domain and a TRH-1 domain within the larger cystatin domain, which may impart significant, but different, roles in regulating bone formation, turnover, and repair to the secreted protein and its degradation products. This is supported by the classical observation that spp24 is not pro-osteogenic when implanted in the ectopic bone forming assay, while spp18.5 is (Urist, 1987). We observed significant C-terminal cleavage of bovine spp24 (residues 23 to 204) that gave rise to a two major daughter proteins at 14.5 kDa and 16 kDa. The most common degradation product was the 16 kDa protein [Met(His)$_6$-spp24, residues 23 to 157], while a less abundant 14.5 kDa degradation product [Met(His)$_6$-spp24, residues 23 to 143] was also observed. These cleavages occur between residues 157 and 158 and residues 143 and 144 of native bovine spp-241-203, respectively (Table 4). Sequence comparison suggests that the first 107 residues of the secreted form of spp24, from the N-terminus to the 11-residue phosphoserine-rich domain, are folded into a cystatin-like tertiary structure containing a 5-stranded β-sheet wrapped around a 5-turn α-helix (Hu, 1995). This domain of spp24 has sequence similarity to family 3 cystatins, whose domains are found in kininogen and endogenous antibiotic precursors (Hu, 1995). C-terminal cleavage of parental proteins containing family 3 cystatin domains gives rise to several potent bioactive peptides, including bradykinin, bactenecin, indolicidin, and BacS, suggesting cleavage of the cystatin domain of spp24 would give rise to an N-terminal bioactive protein containing the cystatin domain and a C-terminal fragment containing the last 62 residues of spp24 (Hu, 1995). The cleavage predicted by Hu, et al. (Hu, 1995) would give rise to a daughter protein that is one amino acid residue shorter than the 14.5 kDa cleavage product observed in the MS profile [Met(His)$_6$-spp24 (residues 24 to 143), Tables 3 and 4]. The N-terminal domain of both the predicted (Hu, 1995) and observed (Tables 3 and 4) cleavage products of spp24 would contain the TRH-1 or putative BMP-binding domain (Behnam, 2005). A synthetic N- to C-disulfide bonded cyclic peptide corresponding to the TRH-1 domain of spp24 binds BMP-2 and stimulates the rate and magnitude of BMP-2-mediated ectopic bone formation in vivo (Behnam, 2005), suggesting that the N-terminal domain of the protein is a bioactive moiety, as predicted when it was cloned (Hu, 1995). At that time, however, the significance of BMP- and TGF-β-binding TRH-1 domains had not been identified, and the physiologic function of an N-terminal protein derived from cleavage of spp24 was not apparent. In the future, these putative cleavage proteins will be synthesized by recombinant techniques, thus permitting detailed structure: function studies of the physiological roles of spp24 (residues 24 to 203) and its daughter proteins in vivo and in vitro.

It should be noted that the cleavage of the recombinant protein occurred slowly over time even in the presence of 8 M urea and protease inhibitors at −20° C. (FIG. 5). This suggests that the cleavage sites are extremely labile to proteolysis. When native spp24 was isolated, a significant amount of lower-molecular weight protein and peptides (<14 kDa) co-purified with it (Hu, 1995). In addition, when the 18.5 kDa protein in "BMP/NCP" was isolated, a non-osteogenic 24 kDa protein, as well as lower-molecular weight proteins of mass 17.5 kDa (histone H$_2$B), 17 kDa, and 14 kDa were obtained (Urist, M. R., et al., *Proc. Natl. Acad. Sci. USA*, 81, 371-375 (1984)). Since the native proteins are heavily phosphorylated (Hu,) and contain 15% to 29% carbohydrate (Urist, M. R., et al., Partial purification and characterization of bone morphogenetic protein. In: *Hormonal Control of Calcium Metabolism*, D. Cohn, R. Talmage, and J. L. Mattews (eds.), pp. 307-314. (Excerpta Medica, Netherlands) (1981)), the relationships between them and the recombinant proteins remain to be established. However, expression of (His)$_6$-spp24 in eukaryotic systems, where post-translational modifications similar to those observed in native bone proteins occur, may provide insights into the relationships between the parental protein and its degradation products.

The susceptibility of spp-24 to proteolysis was confirmed by co-incubating the recombinant protein with extracts of mouse (pre)osteoblastic MC3T3-E1 cells. In the absence of calcium, no significant degree of degradation was observed until 24 hr of incubation (FIG. 6). However, in the presence of 4 mM calcium, rapid proteolysis without accumulation of intermediate 14.5 kDa or 16 kDa proteins was observed (FIG. 6). There was essentially complete degradation after 2 hr (FIG. 6). This may explain, in part, why the significant amounts of spp24 that are synthesized in the liver and bound by the mineral phase are not present in intact bone when spp24 is isolated from native bone, which contains only small amounts of the protein. It may also provide insights into the physiological conditions that favor conservation of the protein vs. terminal degradation. Of interest is the observation that one of the two functional cystatin domains of the kininogens (which, like spp-24, are members of the family 3 cystatin family) binds to and inhibits calpains, or calcium-activated cysteine proteases (Abrahamson, M., *Meth. Enzymol.*, 244, 685-700 (1994)). Calpains (calcium-activated papain-like proteases) are abundant proteins in osteoblasts (Tram, K.K.-T., et al., *Biochem. Mol. Biol. Intl.*, 29, 981-987 (1993)) and may be one of the proteolytic enzyme systems that mediate spp24 degradation in the presence of MC3T3-E1 cell extracts and calcium. Experiments are currently underway to identify and characterize the protease(s) that contribute to the proteolytic processing of spp24.

TABLE 3

MS analysis of IMAC-binding Met(His)$_6$-spp24 (residues 24 to 203)-derived proteins in *E. coli* inclusion bodies.

| Observed Mass of Protein (Da)* | Protein Sequence | Comments |
|---|---|---|
| 21455.57 | Met(His)$_6$-spp24 (residues 24 to 203) | N-terminal carbamoylation product** |
| 21423.02 | Met(His)$_6$-spp24 (residues 24 to 203) | $[M + H]^+_{calc}$ = 21434.88. |
| 16034.45 | Met(His)$_6$-spp24 (residues 24 to 157) | This is the major degradation product. $[M + H]^+_{calc}$ = 159996.7; N-term. carbamoylated $[M + H]^+_{calc}$ = 16039.7. |
| 14554.34 | Met(His)$_6$-spp24 (residues 24 to 143) | This is a less abundant degradation product. $[M + H]^+_{calc}$ = 14511.2; N-terminally carbamoylated $[M + H]^+_{calc}$ = 14554.2. |

*Protein masses are expressed as $[M + H]^+$. Where the spectrum of two peaks could not be resolved, the centroided mass is noted.
**The calculated mass for Met(His)$_6$-spp24 (residues 24 to 203) is 21,434.88 Daltons. The carbamoyl group adds 43 Da. The mass of the carbamoylated full-length construct would be 21,477.88 Da.

TABLE 4

Cleavage sites identified in recombinant bovine Met(His)$_6$-spp24 (residues 24 to 203). The amino acid residues in the N-terminal Met(His)$_6$ tag are not numbered. The subscript numbers indicate the residue numbers in bovine spp24 (residues 24-203). The first residue (residue 24) is not numbered. Solid wedges indicate cleavage sites of the 14.5 kDa and 16 kDa cleavage proteins, respectively, identified by MS in IMAC fractions.

| | | | |
|---|---|---|---|
| MHHHHHH (SEQ ID NO: 15) | FPVYDYD$_{30}$ (SEQ ID NO: 16) | PASLKEALSA$_{40}$ (SEQ ID NO: 17) | SVAKVNSQSL$_{50}$ (SEQ ID NO: 18) |
| SPYLFRAFRS$_{60}$ (SEQ ID NO: 19) | SVKRVNALDE$_{70}$ (SEQ ID NO: 20) | DSLTMDLEFR$_{80}$ (SEQ ID NO: 21) | IQETTCRRES$_{90}$ (SEQ ID NO: 22) |
| EADPATCDFQ$_{100}$ (SEQ ID NO: 23) | RGYHVPVAVC$_{110}$ (SEQ ID NO: 24) | RSTVRMSAEQ$_{120}$ (SEQ ID NO: 25) | VQNVWVRCHW$_{130}$ (SEQ ID NO: 26) |
| SSSSGSSSSE$_{140}$ (SEQ ID NO: 27) | EMF▲FGDILGS$_{150}$ (SEQ ID NO: 28) | STSRNSY▲LLG$_{160}$ (SEQ ID NO: 15) | LTPDRSRGEP$_{170}$ (SEQ ID NO: 29) |
| LYEPSREMRR$_{180}$ (SEQ ID NO: 30) | NFPLGNRRYS$_{190}$ (SEQ ID NO: 31) | NPWPRARVNP$_{200}$ (SEQ ID NO: 32) | GFE$_{203}$ | are critical to skeletal homeostasis in post-natal life. Recombinant human BMP-2 (rhBMP-2) is well accepted as an osteoinductive therapeutic which is used to promote bone healing in fracture non-unions and spine fusion in degenerative disc diseases. BMPs can be significant in pathological processes such as skeletal metastasis.

Secreted phosphoprotein 24 kD (spp24) is a bone matrix protein which binds proteins of the TGF-β family through a region that is similar to the TGF-β receptor II (TRH1 domain) (Behnam, 2005). Full-length spp24 strongly inhibits BMP-2 induced bone formation when tested in an ectopic bone forming assay (Sintuu, 2008). Smaller forms of spp24 produced through proteolysis are less inhibitory of BMP-2 induced bone formation (Brochmann E J, et al., J Orthop Res 2010; 28:1200-7) which has lead to the hypothesis that regulated proteolysis of spp24 is one mechanism through which the availability of BMPs is regulated in skeletal tissue (Brochmann, 2009).

Cell line A549 is a well characterized human non-small cell lung carcinoma line that expresses BMP-2 and responds to this autocrine secretion with increased growth. Previous investigations have shown that noggin, an inhibitor of BMPs, can be employed to reduce tumor growth in this model of skeletal metastasis (Feeley B T, et al., J Bone Min Res 2006; 21:1571-1580).

In summary, BMPs and TGF-β contribute to the growth of some skeletal metastases through autocrine stimulation. Spp24 has been shown to bind to both BMP-2 and TGF-β and to markedly inhibit the osteogenic properties of rhBMP-2. The studies in this example would show that addition of spp24 would sequester autocrine growth factors (especially BMP-2) and reduce tumor growth in a system where autocrine stimulation by BMP-2 is known to be important. Further, since the studies in this example would show that spp24 could be used to bind to and sequester BMP-2 (and other related cytokines) and through this interruption of autocrine stimulation decrease tumor growth. The compositions of invention therefore would have applications in the orthopaedic management of metastatic disease.

In the studies described in this exmaple, in vitro and in vivo study using the A549 human non-small cell lung cancer cell line, recombinant human bone morphogenetic protein-2 (rh-BMP-2), and secreted phosphoprotein 24 kD (spp24), a protein that binds members of the Transforming Growth Factor-beta (TGF-β) family of cytokines Cellular proliferation of Example 2

Studies on Tumor Suppression by SPP24

Introduction

Bone morphogenetic protein-2 (BMP-2) is a member of the transforming growth factor-beta (TGF-β) family of proteins. These proteins perform a variety of pattern specifying and morphogenic functions in the mammalian embryo and A549 cells was measured in vitro in the presence and absence of BMP-2 and spp24. A549 cells were injected into two sites (subcutaneous and intraosseus) in SCID mice with and without the co-injection of BMP-2 and spp24. Tumor growth after 8 weeks was assessed through gross examination, radiological imaging, and histological analysis.

Materials and Methods

In Vitro Studies

Cell Culture and Cell Proliferation Assay

The human non-small cell lung cancer (NSCLC) cell line A549 was used in this study (ATCC, Manassas, Va., USA). A549 cells were maintained in DMEM with 10% FBS and antibiotics (Fisher scientific, Pittsburgh, Pa.) in a humidified incubator with 5% CO2 at 37° C. Cells were not used beyond 10 passages. Cells were plated in serum free medium at a density of 10,000 cells/well and allowed to attach for 24 h. RhBMP-2 (INFUSE®, Medtronic Sofamor Danek, Minneapolis, Minn.) was added to fresh serum-free media at final concentrations of 0, 1, 10, 50, 100, and 500 ng/ml. Recombinant spp24 was prepared as described previously (Murray E J B, et al., Connect Tiss Res 2007; 48:1-8) and added in serum-free media to final concentrations of 10, 25, 50, 75 μg/ml. Cells were incubated for 48 h before cell proliferation was assessed using Quick Cell Proliferation Assay (BioVision, Mountain View, Calif., USA) according to manufacturer's recommendations. Results were reported as a percentage compared with untreated cells.

In Vivo Studies

Animals and Experimental Groups

Forty, eight-week-old male SCID mice (weight 23.5 to 29.1 g, mean 27.1 g) were housed under pathogen-free conditions in accordance with the protocol approved by the Chancellor's Animal Research Committee (ARC) at the University of California, Los Angeles. There were four experimental groups in this study, and each group underwent implantation of cells in both a subcutaneous model and an intra-tibial injection. Group I animals received A549 cells alone as a control group. Group II animals received A549 cells+rhBMP-2 (10 μg/10 μl). Group III received an A549 cells+spp24 (1000 μg). Group IV received an A549 cells+rhBMP2+spp24. There were 10 animals in each group.

Subcutaneous Implantation and Direct Measurement of Tumor Size

A549 cells ($1\times10^5$) were suspended in 15 μl of 1×PBS and 15 μl Affi-Gel Blue (BioRad Laboratories, Hercules, Calif.) and injected into the subcutaneous space on the backs of mice. Briefly, after the SCID mice were anesthetized, then maintained via an isoflurane face mask, the overlying skin was prepped in sterile fashion with 70% ethanol and betadine. Different materials and A549 cells were then injected into the subcutaneous space on the backs of SCID mice. Animals were killed at 8 weeks or earlier if large tumor size exceeded that permitted by the ARC protocol and the tumor removed. Tumors were measured in three dimensions (length×width×depth). These measurements were repeated by three observers blinded to treatment group. Results are reported in millimeters as mean±SE.

Intratibial Implantation and Rediographic Analysis

Tibial implantation of A549 cells plus experimental materials was performed as previously described.[14,15] Mice were anesthetized with isoflurane, then maintained via an isoflurane face mask. The overlying skin was prepped in a sterile fashion with 70% ethanol and betadine. A 3-mm longitudinal incision was made over the patellar ligament with a no. 11 scalpel blade and a 2-mm longitudinal incision was then made along the medial border of the patellar ligament to the tibial plateau. A 27.5-gauge needle was introduced through the proximal tibial plateau and into the proximal tibia. Thirty microliters of a suspension containing $1\times10^5$ A549 cells in 15 H.1 of 1×PBS with 15 μl of Affi-Gel Blue containing the appropriate test materials was injected into the cavity. The wound was closed with a single 5-0 Vicryl suture. At 8 weeks, prior to their sacrifice, animals were anesthetized as previously described, and radiographs were obtained using a Faxitron X-ray cabinet (Faxitron, Inc. Lincolnshire, Ill.). Three independent observers blinded to the treatment groups evaluated the radiographs for the presence of osteoblastic and osteolytic lesions. Radiographs were scored as follows: 0-normal; 1-lytic lesion present within the medullary canal only; 2-obliteration of one cortex; 3-obliteration of two cortices.

Histologic and Histomorphometric Analysis

Animals were killed at 8 weeks (or earlier if required by an excessive tumor size) and both the soft tissue tumor and the hind limb were harvested for histological analysis. Soft tissue tumors were fixed in 10% buffered formalin. The tibias were fixed in 10% buffered formalin followed by decalcification in a solution of 10% EDTA for 2 weeks at room temperature with gentle stirring. Longitudinal sections of the proximal tibia were prepared and stained with H&E. For histologic and histomorphometric analyses, all microscopic slides were scanned with a ScanScope GL (Aperio Technologies, Inc., Vista, Calif.) equipped with a 20× objective. The following parameters were considered in the qualitative analysis: amount of tumor cells between cortices from the proximal tibia; anterior and posterior cortical destruction and remodeling; new bone formation within the medullary canal; and anterior/posterior extension of bone formation outside the medullary canal. These histologic findings were graded with the following scale: 0 (none), 1 (mild), 2 (moderate), 3 (intense). Bone volume and tumor volume, expressed as a percentage of total tissue volume (% BV/TV and % TuV/TV, respectively) were quantified in whole-slide images using Spectrum software (Aperio Technologies, Inc. Vista, Calif.).

Statistical Analysis

For measurements of tumor size, radiographic scores of intratibial tumors, and histomorphometric parameters, means were compared using Student's t-test. The subcutaneous tumor size and radiographic data were also assessed with a kappa statistic calculated to determine interobserver agreement. $p<0.05$ was considered to be statistically significant.

Results

Effects of rhBMP-2 and spp24 on A549 Cell Proliferation In Vitro

The results of the in vitro studies on the effects of BMP-2 and spp24 on A549 cell proliferation are shown in FIG. 7. BMP-2 significantly increased proliferation in a dose-dependent manner at doses of the 0, 1, 10, and 50 ng/ml. Higher doses (50 and 500 ng/ml) were associated with a decline in proliferation rates towards those of the cells alone group. The addition of spp24 to the BMP treatment resulted in an attenuation of the BMP affect at all doses. Treatment of the cells with spp24 alone resulted in a slight dose-dependent inhibition of proliferation.

Effects of rhBMP-2 and spp24 on Subcutaneous Tumor Formation

The results of measurements of tumor size following subcutaneous injection of A549 cells with the various treatments are shown in FIG. 8. Addition of rhBMP-2 increased tumor volume by about 3 fold. Animals implanted with A549 cells+rhBMP2 (558.4±590.7 mm3) had a significantly larger subcutaneous tumor volume compared with that of A549 cells alone (127.4±117.5 mm3) (p=0.041). On the other hand, addition of spp24 dramatically reduced tumor volume in both the group that was treatment with exogenous BMP and the group where cells were delivered with only spp24. Tumor volumes for the Cell+BMP+SPP group (14.3±25.1 mm3) and the Cell+SPP group (12.6±21.6 mm3) were significantly smaller that that of the Cell Alone group (127.4±117.5 mm3) (p=0.028 and 0.027, respectively).

FIG. 8 shows subcutaneous tumor formation eight weeks after injection of A549 human non-small cell lung cancer cells co-injected with rhBMP-2, spp24, both rhBMP-2 plus spp24 or vehicle alone. p Values for critical comparisons: cells+rhBMP-2 v. cells alone (p=0.041); cells+spp24 v. cells alone (p=0.027); cells+rhBMP-2+spp24 v. cells alone (p=0.028); cells+rhBMP-2+spp24 v. cells+rhBMP-2 (p=0.048). Images illustrate representative tumors at necropsy. For numerical analysis of measurements from all tumors Radiographic Analyses of rhBMP-2 and spp24 on Intratibial Tumor Formation Radiographs of injected tibias were obtained at the time of death and evaluated by three independent observers who were blinded with respect to treatment groups. There was excellent overall agreement between readers with a kappa statistic of 0.89. These results are presented in FIG. 9.

Eight of 10 animals that had A549 cells alone implanted in their tibias formed an osteoblastic/osteolytic lesion in the proximal tibia. The average radiographic score at 8 weeks was 2.1+1.1 (range, 1-3). Nine of 10 Animals that had A549 cells+rhBMP-2 implanted in their tibias also formed an osteoblastic/osteolytic lesion by 8 weeks. The average radiographic score was 2.4±1.1 (range, 1-3; p=0.277 versus A549 cells alone). In contrast, there was minimal new bone formation found in three of ten animals treated with A549+spp24. The average radiographic score for these subjects was 0.5±0.6 (range, 0-2; p=0.005 versus A549 cells alone). Similarly, the average radiographic score of the animals treated with A549+rhBMP2+spp24 was 0.7±0.7 (range, 0-2; p=0.027 versus A549 cells alone). Finally, the mean radiographic score for the Cell+BMP+SPP group was significantly lower than that of the Cell+BMP group (p=−0.006).

Figure 9:
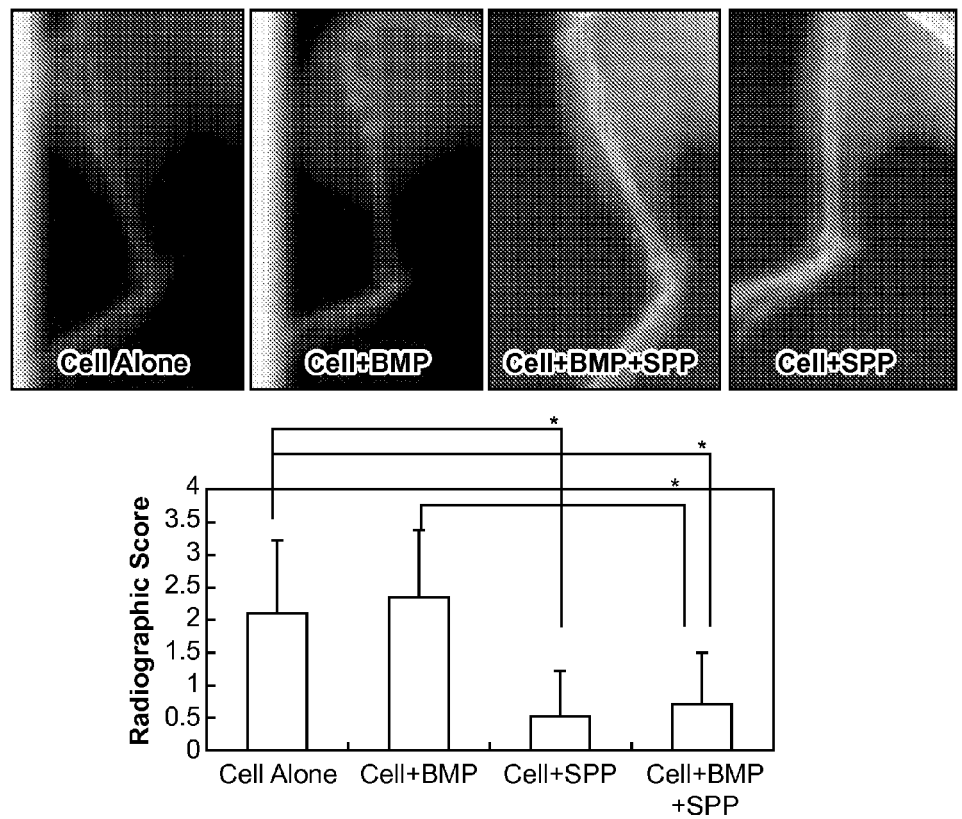
FIG. 9 are radiographs illustrating intratibial tumor formation eight weeks after injection of A549 human non-small cell lung cancer cells co-injected with rhBMP-2, spp24, both rhBMP-2 plus spp24 or vehicle alone.

FIG. 9 shows intratibial tumor formation eight weeks after eight weeks after injection of A549 human non-small cell lung cancer cells co-injected with rhBMP-2, spp24, both rhBMP-2 plus spp24 or vehicle alone. Comparisons with significant differences (p<0.05) are indicated with an asterisk. Radiographs illustrate representative findings at the time of necropsy.

Histologic and Histomorphometric Anaylses

Specimens from the cells alone and the cells plus rhBMP-2 treatment groups showed abundant masses of adenocarcinoma cells in both the subcutaneous (FIG. 10) and intratibial (FIG. 11) sites whereas those from the Cell+SPP and the Cell+BMP+SPP groups revealed only a few scattered tumor cells.

The histologic parameters considered in the qualitative analysis are presented in Table 5. There was significantly more anterior and posterior cortical destruction in the tibias of subjects that received A549 cells alone and subjects that received A549 cells plus rhBMP-2 compared to subjects in either treatment group that received spp24. There was no significant difference between groups in with respect to new bone formation, amount of trabecular bone in the medullary canal and extension of bone formation outside the canal.

Table 6 shows the calculated results for the % TuV/TV (the proportion of tumor volume to total tissue volume in a longitudinal section of the proximal tibia at midline) and the % Bv/Tv (the proportion of total mineralized trabeculae volume in the total tissue volume in the section) from the specimens in this study. Animals that were injected with A549 cells plus rhBMP2 had the highest tumor volume but this value was not significantly greater than that of the A549 cells alone group. Both of these groups had higher relatively tumor volumes than those of either group that received spp24 but there was insufficient tumor mass in the specimens from the groups that received spp24 to allow for quantitative analysis.

Figure 10:
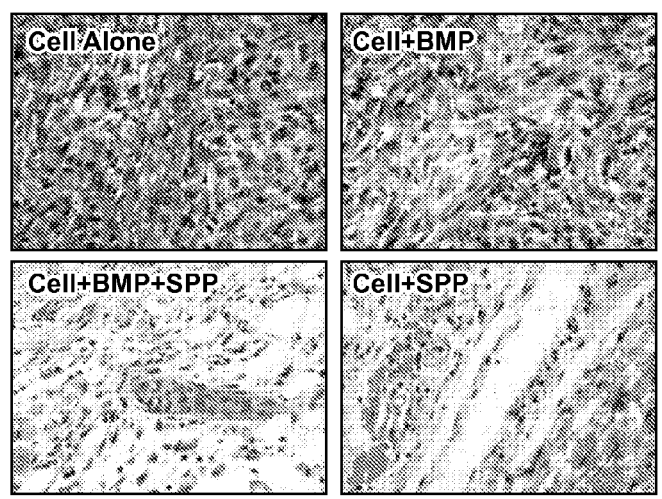
FIG. 10 shows representative histological sections of subcutaneous tumors eight weeks after injection of A549 human non-small cell lung cancer cells co-injected with rhBMP-2, spp24, both rhBMP-2 plus spp24 or vehicle alone.

FIG. 10 shows representative histological sections of subcutaneous tumors eight weeks after injection of A549 human non-small cell lung cancer cells co-injected with rhBMP-2, spp24, both rhBMP-2 plus spp24 or vehicle alone. Original magnification 400×.

Figure 11:
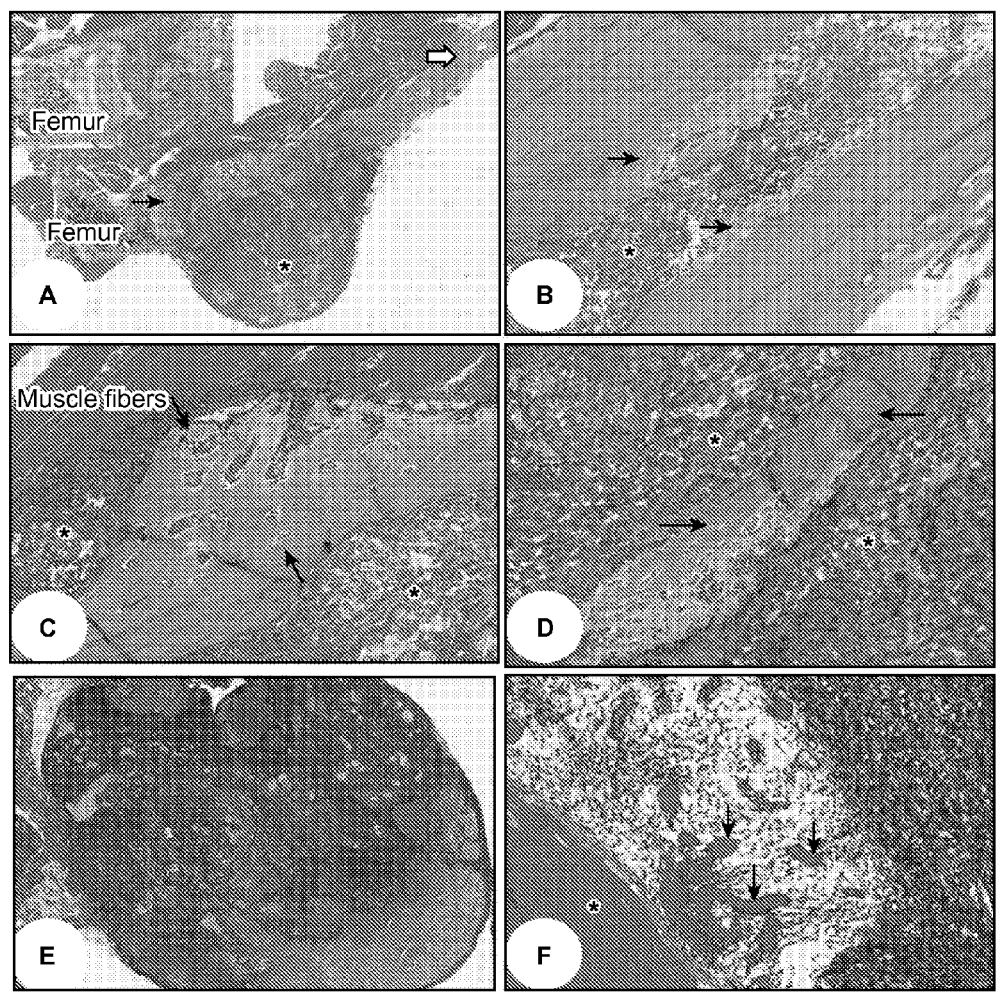
FIG. 11 shows histologic analyses of intratibial tumors eight weeks after injection of A549 human non-small cell lung cancer cells.

FIG. 11 shows histologic analyses of intratibial tumors eight weeks after injection of A549 human non-small cell lung cancer cells. Animals treated with A549 cells alone and A549 cells+rhBMP-2 showed significant tumor formation in the proximal tibia. A: Panoramic view of a longitudinal section showing the distal femur (far left) and the proximal tibia with a huge tumor mass (asterisk) that extends outside the tibial cortex between the proximal metaphysis (arrow) and diaphysis (block arrow). Insert in upper left shows high power view of the knee joint; B: New corticoendosteal bone formation in association with occupation of the intramedullary canal by infiltrating tumor cells (asterisk); C: New subperiosteal bone formation (arrows) associated with tumor invasion of muscular tissue and the medullary canal (asterisks); D: New (woven) bone formation (arrows) within the tumor mass (asterisks); E: Hemorrhage and necrotic areas within a large tumor mass; F: Peritumoral angiogenesis (arrows) seen between normal muscle fibers (asterisk) and tumor cells.

Discussions

The vertebral column is the most common site of skeletal metastases (Harrington, I. D: et al., J Bone Joint Surg Am 1986; 68:1110-1115). Metastases from primary tumors of the lungs, prostate, breasts, kidneys, thyroid, and gastrointestinal tract account for the majority of spinal column tumors. Improvements in oncological treatment including adjuvant therapies and more aggressive resection have increased survival time in patients with spinal tumors. Although many tumors are not curative, resection and stabilization can have beneficial effects on neurological status, function, pain, and mobility (see, e.g., Boden, S D, Schimandle J H. Fusion. Biology of lumbar spine fusion and bone graft materials. In: International Society for Study of the Lumbar Spine Editorial Committee, editors. The lumbar spine, $2^{nd}$ ed. Philadelphia: WB Saunders, 1996:1284-306).

Many research reports indicate that BMPs are expressed in a variety of carcinoma cell lines and tumors originating from multiple organs including tumors of lung (e.g., Langenfeld, E M, et al., Carcinogenesis 2003; 24:1445-1454) prostate (see, e.g., Masuda, H, et al., Prostate 2003; 54:268-74) breast (see, e.g., Pouliot F, et al., J Endocrinol 2000; 172:187-198) and kidney (Kim, I Y, et al., Clin Cancer Res 2003; 9(16 Pt 1):6046-6051). While not all reports have shown a proliferation enhancing effect of BMPs (see, e.g., Orui, H, et al., J Orthop Sci 2000; 5:600-604) in general, expression profiling has demonstrated that tumor cells with osteoblastic characteristics secrete cytokines in the BMP/TGF-beta family that increase osteoblastogenesis and bone formation, including BMPs-2, -4, -6, and -7 and TGF-beta (see, e.g., Lee, Y, et al., J Orthop Res 2003; 21:62-72). Osteoblastic tumor cells express mRNA and protein for BMP receptors, and exogenous BMPs stimulate tumor cell cellular migration and invasion in vitro and in vivo (Feeley, B T, et al., J Bone Miner Res. 2005; 20:2189-2199). These results suggest, therefore, that BMP/TGF-f3 cytokines are important in the development of metastatic osteoblastic lesions and that inhibition of their activity would effectively limit tumor growth.

Secreted phosphoprotein 24 kD (spp24) is a bone matrix protein which binds proteins of the TGF-β family through a region that is similar to the TGF-β receptor II (TRH1 domain) (Behnam, 2005) and inhibits the osteogenic activity of BMP-2 (see, e.g., Brochmann, 2009). This protein exits in bone tissue in several proteolytic size forms which effect BMP-2 activity differently (Brochmann, 2009). Interestingly, spp24 shares sequence and physico-chemical properties with pro-osteogenic proteins described decades ago by two investigators (Urist and Sen) (Brochmann, 2009) and a BMP enhancing therapeutic peptide has been developed which is based on the sequence of the BMP/TGF-beta binding region of spp24 (Behnam, 2005).

In the present report, the in vitro studies showed that rhBMP-2 increased A549 human non-small cell lung cancer cell growth up to a maximal effect at 50 ng/ml. Higher doses were associated with less enhancement of proliferation indicating that the effects of BMP-2 on proliferation may vary with cell culture conditions. This may help to explain the disparity of the responses reported, especially those showed an inhibition of proliferation (Soda, H, et al., Anti-Cancer Drugs 1998; 9:327-331; and Orui, H., et al. J Orthop Sci 2000; 5:600-604). Our studies confirmed the finding that rhBMP-2 enhances tumor growth of A549 cells in both subcutaneous and intraosseus site, as previously reported (Feeley, B T, et al., J Bone Min Res 2006; 21:1571-1580). In both sites, co-injection of spp24 with rhBMP-2 ameliorated the effect of the BMP-2. Addition of spp24 (without BMP-2) to A549 cells in vitro resulted in reduced proliferation. We believe, but are not bound by, that this was due to sequestration of endogenous BMPs which are required for autocrine stimulation though we cannot completely rule out a less specific effect. Similarly, the addition of spp24 to BMP-2 in the in vivo models ameliorated the tumor growth enhancing effects of the BMP in both the subcutaneous and intratibial sites. Furthermore, co-injection of spp24 (without BMP) with A549 cells markedly inhibits tumor growth in vivo at both soft tissue and the intraosseus sites. In this regard, spp24 had an effect that was similar to that of noggin (e.g., Feeley, 2006).

The current therapies for metastatic cancer in bone include hormone treatment (which is ineffective against androgen- or estrogen-independent tumors), external beam radiation (with corticosteroids or surgical decompression of spinal metastases), radioisotopes, prophylactic surgery for osteolytic lesions with impending fracture, bisphosphonates or RANK/RANKL system inhibitors (e.g. osteoprotegerin) for osteolytic bone lesions, and growth factor, growth factor receptor or cell adhesion protein antagonists (Canalis, E, et al., Endo Rev 2003; 24:218-235). The limitations of these approaches include toxicity, specificity (osteolytic vs. osteoblastic lesions), cost, and the potential for adverse side effects (Canalis, 2003). The therapeutic potential of broad-spectrum BMP/TGF-beta cytokine growth factor antagonists, such as spp24, has not been fully exploited. If the pro-osteogenic effects of TGF-beta/BMP cytokines on metastatic osteoblastic lesions in bone can be inhibited with a highly-specific, inexpensive, non-toxic native binding protein, such as spp24, it could lead to the development of a new class of therapeutic agents that could reduce morbidity and improve the quality of life for cancer patients.

CONCLUSIONS

Spp24 can reduce A549 cell tumor growth in both soft tissue and intraosseus environments. We believe, but are not bound by, that the mechanism for this inhibition is interruption of autocrine stimulation through the sequestration of BMP-2. Spp24 can be developed into a therapeutic agent that can be employed in clinical situations where the inhibitions of BMPs and related proteins are advantageous.

TABLE 5

Histologic analysis of tibiae

| Parameters* | Cells only (A) | Cells + spp24 (B) | Cell + rhBMP-2 (C) | Cells + rhBMP-2 + spp24 (D) |
|---|---|---|---|---|
| Amount of tumor cells between cortices (1) | 2.67 (2.13-3.21) | 0 (0-0) | 3.0 (3.0-3.0) | 0 (0-0) |
| Anterior cortex destruction (2) | 2.33 (1.06-3.60) | 0 (0-0) | 3.0 (3.0-3.0) | 0 (0-0) |
| Posterior cortex destruction (3) | 2.33 (1.79-2.88) | 0 (0-0) | 3.0 (3.0-3.0) | 0 (0-0) |
| New bone formation within the medullary canal (4) | 0.41 (−0.10-0.93) | 0 (0-0) | 0.50 (−0.31-1.31) | 0 (0-0) |
| Extension of bone formation outside the medullary canal (5) | 0.58 (0.07-1.10) | 0 (0-0) | 0.83 (0.40-1.26) | 0 (0-0) |

*Parameters were graded as follows: 0 (none), 1 (mild), 2 (moderate), 3 (intense). Values shown as mean (95% C.I.).

P values for pairwise comparisons with Mann-Whitney U test:

Parameter (1): A v. B: 0.002; A v. C, 0.394; A v. D: 0.002; B v. C, 0.002; C v. D: 1.0

Parameter (2): A v. B: 0.015; A v. C, 0.394; A v. D: 0.015; B v. C, 0.002; C v. D: 1.0

Parameter (3): A v. B: 0.002; A v. C, 0.065; A v. D: 0.002; B v. C, 0.002; C v. D: 1.0

Parameter (4): A v. B: 0.180; A v. C, 0.937; A v. D: 0.180; B v. C, 0.180; C v. D: 1.0

Parameter (5): A v. B: 0.065; A v. C, 0.394; A v. D: 0.065; B v. C, 0.015; C v. D: 1.0

TABLE 6

Quantitative histomorphometric analysis of tibiae

| Parameter | Cells only (A) | Cells + spp24 ** (B) | Cells + rhBMP-2 (C) | Cells + rhBMP-2 + spp24 ** (D) |
|---|---|---|---|---|
| % TuV/TV * (1) | 35.6 (20.6-50.6) | insufficient | 58.3 (41.9-74.8) | insufficient |
| % BV/TV * (2) | 3.11 (0.062-6.17) | insufficient | 1.30 (0.23-2.37) | insufficient |

* %TuV/TV: TUMOR VOLUME/TOTAL VOLUME; Proportion of tumor volume to total tissue volume in a longitudinal section of the proximal tibia at midline. % BV/TV: BONE VOLUME/TOTAL VOLUME; Proportion of total mineralized new formed bone in the total section.
** There was insufficient tumor mass in specimens from these groups to permit quantitative analysis.

P values from comparisons from Mann-Whitney U test:

Parameter (1): A v. C, 0.065

Parameter (2): A v. C, 0.485

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A composition, comprising a peptide fragment of secreted phosphoprotein 24 kD (spp24) (SEQ ID NO:1) that specifically binds BMP-2,
   wherein said peptide fragment consists of amino acids 80-129 of spp24 or amino acids 110-128 of spp24.

2. The composition of claim 1, in a local delivery formulation.

3. The composition of claim 1, in a systemic delivery formulation.

4. The composition of claim 2, wherein the local delivery formulation comprises a patch.

5. The composition of claim 1, further comprising a pharmaceutically acceptable carrier.

6. The composition of claim 2, wherein the local delivery formulation is suitable for injection.

7. The composition of claim 2, wherein the local delivery formulation comprises a sustained release formulation.

8. The composition of claim 1, wherein said peptide fragment is present in an amount effective to achieve a serum concentration of 0.01 nM to 1,000,000 nM.

* * * * *